(12) United States Patent
Jonn et al.

(10) Patent No.: US 11,413,370 B2
(45) Date of Patent: *Aug. 16, 2022

(54) ADHESIVE-CONTAINING WOUND CLOSURE DEVICE AND METHOD

(71) Applicant: Ethicon, Inc., Somerville, NJ (US)

(72) Inventors: Jerry Y. Jonn, Raleigh, NC (US); Julian Quintero, Flemington, NJ (US); Glenn Hoskin, Apex, NC (US)

(73) Assignee: Ethicon, Inc., Raritan, NJ (US)

(*) Notice: Subject to any disclaimer, the term of this patent is extended or adjusted under 35 U.S.C. 154(b) by 188 days.

This patent is subject to a terminal disclaimer.

(21) Appl. No.: 16/556,443

(22) Filed: Aug. 30, 2019

(65) Prior Publication Data

US 2019/0381207 A1 Dec. 19, 2019

Related U.S. Application Data

(63) Continuation of application No. 15/964,538, filed on Apr. 27, 2018, now Pat. No. 10,398,802, which is a continuation of application No. 15/490,176, filed on Apr. 18, 2017, now Pat. No. 10,434,211, which is a continuation of application No. 12/207,984, filed on
(Continued)

(51) Int. Cl.
| | | |
|---|---|---|
| *A61L 24/06* | (2006.01) | |
| *A61F 13/02* | (2006.01) | |
| *A61B 17/00* | (2006.01) | |
| *A61B 17/08* | (2006.01) | |
| *A61L 24/00* | (2006.01) | |

(52) U.S. Cl.
CPC ........ *A61L 24/06* (2013.01); *A61B 17/00491* (2013.01); *A61B 17/085* (2013.01); *A61F 13/0203* (2013.01); *A61F 13/023* (2013.01); *A61L 24/001* (2013.01); *A61L 24/0036* (2013.01); *A61L 24/0042* (2013.01); *A61L 2400/16* (2013.01)

(58) Field of Classification Search
CPC .. A61B 17/085; A61F 13/0246; A61F 13/025; A61F 13/0253; A61F 13/0203; A61F 13/023; A61L 24/06; A61L 24/001; A61L 24/0036; A61L 24/0042; A61L 2400/16
See application file for complete search history.

(56) References Cited

U.S. PATENT DOCUMENTS

| 167,162 A | 8/1875 | French |
|---|---|---|
| 1,656,199 A | 1/1928 | Ensley |

(Continued)

FOREIGN PATENT DOCUMENTS

| AU | 2005-215776 A | 9/2005 |
|---|---|---|
| CA | 2262408 A | 8/2000 |

(Continued)

OTHER PUBLICATIONS

U.S. Appl. No. 10/779,721, filed Feb. 18, 2004, US-20055-0182443-A1, Abandoned.

(Continued)

*Primary Examiner* — Alexander J Orkin

(57) ABSTRACT

A tissue bonding article includes a flexible material, an adhesive substance applied over at least a portion of a bottom side of the flexible material, and a polymerizable adhesive composition permeated throughout at least a portion of the flexible material.

27 Claims, 7 Drawing Sheets

Related U.S. Application Data

Sep. 10, 2008, now Pat. No. 9,655,622, which is a continuation of application No. 10/779,721, filed on Feb. 18, 2004, now abandoned.

(56) References Cited

U.S. PATENT DOCUMENTS

| | | |
|---|---|---|
| 2,399,545 A | 4/1946 | Davis |
| 2,508,855 A | 5/1950 | Brown |
| 2,721,858 A | 10/1955 | Joyner et al. |
| 2,722,220 A | 11/1955 | Mestrand |
| 2,807,262 A | 9/1957 | Lew |
| 2,905,174 A | 5/1959 | Smith |
| 3,085,572 A | 4/1963 | Blackford |
| 3,254,111 A | 5/1966 | Hawkins et al. |
| 3,402,716 A | 9/1968 | Baxter |
| 3,520,300 A | 7/1970 | Flower, Jr. |
| 3,731,683 A | 5/1973 | Zaffaroni |
| 3,888,247 A | 6/1975 | Stenvall |
| 3,940,362 A | 2/1976 | Overhults |
| 3,983,878 A | 10/1976 | Kawchitch |
| 3,995,641 A | 12/1976 | Kronenthal et al. |
| 4,068,664 A | 1/1978 | Sharp et al. |
| 4,080,348 A | 3/1978 | Korpman |
| 4,126,130 A | 11/1978 | Cowden et al. |
| 4,140,115 A | 2/1979 | Schonfeld |
| 4,263,906 A | 4/1981 | Finley |
| 4,313,865 A | 2/1982 | Teramoto et al. |
| 4,340,043 A | 7/1982 | Seymour |
| 4,364,876 A | 12/1982 | Kimura et al. |
| 4,390,519 A | 6/1983 | Sawyer |
| 4,460,369 A | 7/1984 | Seymour |
| 4,560,723 A | 12/1985 | Millet et al. |
| 4,584,355 A | 4/1986 | Blizzard et al. |
| 4,585,836 A | 4/1986 | Homan et al. |
| 4,591,622 A | 5/1986 | Blizzard et al. |
| 4,612,230 A | 9/1986 | Liland et al. |
| 4,614,183 A | 9/1986 | McCracken et al. |
| 4,630,603 A | 12/1986 | Greenway |
| 4,655,767 A | 4/1987 | Woodard et al. |
| 4,671,266 A | 6/1987 | Legnyel et al. |
| 4,720,513 A | 1/1988 | Kameyama et al. |
| 4,728,380 A | 3/1988 | Jones et al. |
| 4,733,659 A | 3/1988 | Edenbaum et al. |
| 4,767,401 A | 8/1988 | Seiderman |
| 4,793,887 A | 12/1988 | Card et al. |
| 4,793,888 A | 12/1988 | Card et al. |
| 4,795,435 A | 1/1989 | Steer et al. |
| 4,852,571 A | 8/1989 | Gadsby et al. |
| 4,867,747 A | 9/1989 | Yarger |
| 4,872,450 A | 10/1989 | Austad |
| 4,950,282 A | 8/1990 | Beisang et al. |
| 4,966,605 A | 10/1990 | Thieler |
| 4,999,235 A | 3/1991 | Lunn et al. |
| 5,035,687 A | 7/1991 | Sandbank |
| 5,059,424 A | 10/1991 | Cartmell et al. |
| 5,086,763 A | 2/1992 | Hathman |
| 5,088,483 A | 2/1992 | Heinecke |
| 5,106,362 A | 4/1992 | Gilman |
| 5,125,907 A | 6/1992 | Philpott |
| 5,164,444 A | 11/1992 | Bernard |
| 5,173,302 A | 12/1992 | Holmblad et al. |
| 5,232,958 A | 8/1993 | Mallya et al. |
| 5,254,132 A | 10/1993 | Barley et al. |
| 5,259,835 A * | 11/1993 | Clark .......... A61F 13/0246 602/48 |
| 5,266,371 A | 11/1993 | Sugii et al. |
| D347,059 S | 5/1994 | Mota |
| 5,308,313 A | 5/1994 | Karami et al. |
| 5,328,687 A | 7/1994 | Leung et al. |
| 5,336,209 A | 8/1994 | Porzilli |
| 5,415,626 A | 5/1995 | Goodman et al. |
| 5,429,592 A | 7/1995 | Jensen |
| 5,445,597 A | 8/1995 | Clark et al. |
| 5,449,340 A | 9/1995 | Tollini |
| D363,126 S | 10/1995 | Dusek |
| 5,456,660 A | 10/1995 | Reich et al. |
| 5,476,440 A | 12/1995 | Edenbaum |
| 5,486,547 A | 1/1996 | Matsuda et al. |
| D370,258 S | 5/1996 | Newman |
| D373,750 S | 9/1996 | Gunderson |
| 5,571,079 A | 11/1996 | Bello et al. |
| 5,575,997 A | 11/1996 | Leung et al. |
| 5,582,834 A | 12/1996 | Leung et al. |
| 5,599,858 A | 2/1997 | Buchanan et al. |
| 5,620,702 A | 4/1997 | Podell et al. |
| 5,623,011 A | 4/1997 | Bernard |
| 5,624,669 A | 4/1997 | Leung et al. |
| D382,343 S | 8/1997 | Wandell et al. |
| 5,653,769 A | 8/1997 | Barley, Jr. et al. |
| D383,211 S | 9/1997 | Dunshee et al. |
| 5,662,599 A | 9/1997 | Reich et al. |
| D387,169 S | 12/1997 | Dunshee et al. |
| D389,244 S | 1/1998 | Dunshee et al. |
| 5,705,551 A | 1/1998 | Sasaki et al. |
| D391,639 S | 3/1998 | Dunshee et al. |
| 5,749,895 A | 5/1998 | Sawyer et al. |
| 5,762,955 A | 6/1998 | Smith |
| 5,780,048 A | 7/1998 | Lee |
| 5,782,788 A | 7/1998 | Widemire |
| 5,823,983 A | 10/1998 | Rosofsky et al. |
| 5,823,986 A | 10/1998 | Peterson |
| D402,371 S | 12/1998 | Haynes et al. |
| D403,425 S | 12/1998 | Hinds et al. |
| D404,139 S | 1/1999 | Young |
| 5,861,348 A | 1/1999 | Kase |
| 5,876,745 A | 3/1999 | Muraoka et al. |
| 5,902,443 A | 5/1999 | Kanakubo et al. |
| 5,928,611 A | 7/1999 | Leung |
| 5,931,800 A | 8/1999 | Rasmussen et al. |
| 5,947,917 A | 9/1999 | Carte et al. |
| 5,951,505 A | 9/1999 | Gilman et al. |
| 5,998,694 A | 12/1999 | Jensen et al. |
| D424,699 S | 5/2000 | Allen |
| 6,093,465 A | 7/2000 | Gilchrist et al. |
| 6,125,265 A | 9/2000 | Yamamoto et al. |
| 6,140,548 A | 10/2000 | Hansen et al. |
| 6,143,352 A | 11/2000 | Clark et al. |
| 6,155,265 A * | 12/2000 | Hammerslag ...... A61B 17/0057 128/898 |
| 6,183,593 B1 | 2/2001 | Narang et al. |
| D439,973 S | 4/2001 | Choksi |
| 6,217,603 B1 | 4/2001 | Clark et al. |
| 6,238,692 B1 | 5/2001 | Smith |
| 6,245,960 B1 | 6/2001 | Eaton |
| 6,284,941 B1 | 9/2001 | Cox et al. |
| 6,310,166 B1 | 10/2001 | Hickey et al. |
| 6,329,564 B1 | 12/2001 | Lebner |
| 6,352,704 B1 | 3/2002 | Nicholson et al. |
| D458,687 S | 6/2002 | Dale et al. |
| 6,410,818 B1 | 6/2002 | Oyaski |
| 6,439,789 B1 | 8/2002 | Balance et al. |
| D463,564 S | 9/2002 | Siegwart et al. |
| 6,455,064 B1 * | 9/2002 | Narang ............. A61K 9/0014 424/443 |
| 6,479,725 B1 | 11/2002 | Brothers |
| 6,482,431 B2 | 11/2002 | Smith |
| 6,512,023 B1 | 1/2003 | Malofsky |
| D471,984 S | 3/2003 | Dunshee et al. |
| D472,319 S | 3/2003 | Oltmann |
| 6,559,350 B1 | 5/2003 | Tetreault et al. |
| 6,579,469 B1 | 6/2003 | Nicholson et al. |
| 6,582,713 B2 | 6/2003 | Newell et al. |
| D477,076 S | 7/2003 | Wall |
| 6,589,269 B2 | 7/2003 | Zhu et al. |
| 6,595,940 B1 | 7/2003 | D'Alessio et al. |
| 6,596,917 B2 | 7/2003 | Oyaski |
| 6,599,318 B1 | 7/2003 | Gabbay |
| 6,620,846 B1 | 9/2003 | Jonn et al. |
| D480,879 S | 10/2003 | Boehm et al. |
| 6,632,450 B1 | 10/2003 | Gregory |
| 6,635,272 B2 | 10/2003 | Leaderman |
| 6,652,559 B1 | 11/2003 | Tetreault et al. |
| 6,667,051 B1 | 12/2003 | Gregory |
| 6,712,839 B1 | 3/2004 | Lönne |

(56) References Cited

U.S. PATENT DOCUMENTS

| | | |
|---|---|---|
| 6,787,682 B2 | 9/2004 | Gilman |
| 6,837,027 B2 | 1/2005 | Hickey |
| 6,841,716 B1 | 1/2005 | Tsutsumi |
| 6,942,683 B2 | 9/2005 | Dunshee |
| D515,701 S | 2/2006 | Horhota et al. |
| D516,728 S | 3/2006 | Wall |
| D520,639 S | 5/2006 | Dodd et al. |
| 7,041,124 B2 | 5/2006 | Purcell |
| 7,044,982 B2 | 5/2006 | Milbocker |
| 7,066,934 B2 | 6/2006 | Kirsch |
| 7,122,712 B2 | 10/2006 | Lutri et al. |
| 7,144,390 B1 | 12/2006 | Hannigan et al. |
| 7,164,054 B2 | 1/2007 | Mori et al. |
| D548,348 S | 8/2007 | Nash |
| 7,252,837 B2 | 8/2007 | Guo et al. |
| D562,461 S | 2/2008 | Nash et al. |
| 7,371,400 B2 | 5/2008 | Borenstein et al. |
| D574,962 S | 8/2008 | Atkins et al. |
| D580,553 S | 11/2008 | Nash |
| D581,467 S | 11/2008 | Winningham et al. |
| 7,457,667 B2 | 11/2008 | Skiba |
| D582,561 S | 12/2008 | Sachi |
| D584,415 S | 1/2009 | Sachi |
| 7,576,257 B2 | 8/2009 | LaGreca, Sr. |
| D611,156 S | 3/2010 | Dunshee |
| 7,713,463 B1 | 5/2010 | Reah et al. |
| D618,810 S | 6/2010 | Tanigawa et al. |
| D621,052 S | 8/2010 | Kase |
| D621,053 S | 8/2010 | Kase |
| D624,190 S | 9/2010 | Neri |
| D632,398 S | 2/2011 | Bray et al. |
| D636,881 S | 4/2011 | Clemens et al. |
| 7,943,811 B2 | 5/2011 | Da Silva Macedo, Jr. |
| 7,981,136 B2 | 7/2011 | Weiser |
| 7,982,087 B2 | 7/2011 | Greener et al. |
| D646,789 S | 10/2011 | Barth |
| 8,343,606 B2 | 1/2013 | Marchitto et al. |
| 8,353,966 B2 | 1/2013 | Day et al. |
| D676,490 S | 2/2013 | Bratter et al. |
| 8,372,051 B2 | 2/2013 | Scholz et al. |
| D679,098 S | 4/2013 | Ogawa |
| D679,402 S | 4/2013 | Conrad-Vlasak et al. |
| D679,403 S | 4/2013 | Heinecke et al. |
| D679,405 S | 4/2013 | Arbesman |
| D679,819 S | 4/2013 | Peron |
| D679,820 S | 4/2013 | Peron |
| D685,484 S | 7/2013 | Brambilla |
| 8,528,730 B2 | 9/2013 | Grossman |
| D691,730 S | 10/2013 | Smith |
| D692,566 S | 10/2013 | Adoni |
| D693,010 S | 11/2013 | Mosa et al. |
| D694,892 S | 12/2013 | Chan et al. |
| 8,603,053 B2 | 12/2013 | Riesinger |
| D697,216 S | 1/2014 | Chan et al. |
| 8,642,831 B2 | 2/2014 | Larsen et al. |
| 8,663,171 B2 | 3/2014 | Tambourgi et al. |
| D705,429 S | 5/2014 | Cheney et al. |
| D707,829 S | 6/2014 | Chan et al. |
| D708,751 S | 7/2014 | Chan et al. |
| 8,777,986 B2 | 7/2014 | Straehnz et al. |
| D712,045 S | 8/2014 | Thornton |
| D713,534 S | 9/2014 | Manley, Jr. |
| D713,967 S | 9/2014 | Adoni |
| D714,575 S | 10/2014 | Mah |
| 8,884,094 B2 | 11/2014 | Lockwood et al. |
| D718,812 S | 12/2014 | Sukhbaatar |
| 9,000,251 B2 | 4/2015 | Murphy et al. |
| RE45,510 E | 5/2015 | Hisamitsu |
| D728,803 S | 5/2015 | Sinda et al. |
| D745,688 S | 12/2015 | Chan et al. |
| D745,689 S | 12/2015 | Chan et al. |
| D746,479 S | 12/2015 | Arefieg |
| RE45,864 E | 1/2016 | Peron |
| D746,996 S | 1/2016 | Karlsson et al. |
| D750,789 S | 3/2016 | Mackay et al. |
| D757,950 S | 5/2016 | Karlsson et al. |
| 9,339,417 B2 | 5/2016 | Ogawa |
| 9,381,284 B2 | 7/2016 | Cornet et al. |
| 9,440,010 B2 | 9/2016 | Locke |
| 9,492,171 B2 | 11/2016 | Patenaude |
| 9,623,142 B2 | 4/2017 | Jonn et al. |
| D786,350 S | 5/2017 | Nakai et al. |
| D786,351 S | 5/2017 | Nakai et al. |
| D786,352 S | 5/2017 | Nakai et al. |
| D786,353 S | 5/2017 | Nakai et al. |
| D786,972 S | 5/2017 | Nakai et al. |
| 9,655,622 B2 * | 5/2017 | Jonn ............... A61L 24/001 |
| D790,071 S | 6/2017 | Ahsani |
| D824,525 S | 7/2018 | Lacy et al. |
| D833,526 S | 11/2018 | Nakai et al. |
| 10,434,211 B2 * | 10/2019 | Jonn et al. ......... A61F 13/0203 |
| 10,470,935 B2 | 11/2019 | Quintero |
| 2001/0002432 A1 | 5/2001 | Bugge |
| 2001/0028943 A1 | 10/2001 | Mashiko et al. |
| 2001/0037077 A1 | 11/2001 | Wiemken |
| 2002/0018689 A1 | 2/2002 | Badejo et al. |
| 2002/0019652 A1 | 2/2002 | DaSilva et al. |
| 2002/0037310 A1 | 3/2002 | Jonn et al. |
| 2002/0039867 A1 | 4/2002 | Curro et al. |
| 2002/0049503 A1 | 4/2002 | Milbocker |
| 2002/0185396 A1 | 12/2002 | Mainwaring et al. |
| 2002/0192107 A1 | 12/2002 | Hickey |
| 2002/0193721 A1 * | 12/2002 | VanDruff ............... A61B 17/04 |
| | | 602/41 |
| 2003/0031499 A1 | 2/2003 | Heard et al. |
| 2003/0050590 A1 | 3/2003 | Kirsch |
| 2003/0093024 A1 | 5/2003 | Falleiros et al. |
| 2003/0100955 A1 | 5/2003 | Greenawalt et al. |
| 2003/0109819 A1 | 6/2003 | Tsuruda et al. |
| 2003/0125654 A1 | 7/2003 | Malik |
| 2003/0175824 A1 | 9/2003 | Pishko et al. |
| 2003/0220596 A1 | 11/2003 | Dunshee |
| 2003/0225355 A1 | 12/2003 | Butler |
| 2004/0001879 A1 | 1/2004 | Guo et al. |
| 2004/0060867 A1 | 4/2004 | Kriksunov et al. |
| 2004/0106888 A1 | 6/2004 | Lutri et al. |
| 2004/0120849 A1 | 6/2004 | Stewart et al. |
| 2004/0142041 A1 | 7/2004 | MacDonald et al. |
| 2004/0162512 A1 | 8/2004 | Liedtke et al. |
| 2004/0220505 A1 | 11/2004 | Worthley |
| 2005/0015036 A1 | 1/2005 | Lutri et al. |
| 2005/0043820 A1 | 2/2005 | Browning |
| 2005/0085757 A1 | 4/2005 | Santanello |
| 2005/0147457 A1 | 7/2005 | Badejo et al. |
| 2005/0153090 A1 | 7/2005 | Marchitto et al. |
| 2005/0154340 A1 | 7/2005 | Schlussel |
| 2005/0182443 A1 | 8/2005 | Jonn et al. |
| 2005/0208100 A1 | 9/2005 | Weber et al. |
| 2005/0288706 A1 | 12/2005 | Widomski et al. |
| 2006/0009099 A1 | 1/2006 | Jonn et al. |
| 2006/0058721 A1 | 3/2006 | Lebner et al. |
| 2006/0141012 A1 | 6/2006 | Gingras |
| 2006/0173394 A1 | 8/2006 | Stroock et al. |
| 2006/0265005 A1 | 11/2006 | Beese |
| 2007/0106195 A1 | 5/2007 | Marcoux et al. |
| 2007/0218101 A1 | 9/2007 | Johnson et al. |
| 2007/0272211 A1 | 11/2007 | Kassner |
| 2007/0282238 A1 | 12/2007 | Madsen et al. |
| 2007/0299542 A1 | 12/2007 | Mathisen et al. |
| 2008/0051687 A1 | 2/2008 | Rogers |
| 2008/0154168 A1 | 2/2008 | Lutri |
| 2008/0086113 A1 | 4/2008 | Tenney et al. |
| 2008/0109034 A1 | 5/2008 | Mather et al. |
| 2008/0110961 A1 | 5/2008 | Voegele et al. |
| 2008/0167633 A1 | 7/2008 | Vannucci |
| 2008/0228219 A1 | 9/2008 | Weiser |
| 2008/0228220 A1 | 9/2008 | Weiser |
| 2008/0280037 A1 | 11/2008 | Sheridan et al. |
| 2008/0302487 A1 | 12/2008 | Goodman et al. |
| 2009/0074842 A1 | 3/2009 | Hsu |
| 2010/0106120 A1 | 4/2010 | Holm |
| 2010/0198161 A1 | 8/2010 | Propp |
| 2010/0262091 A1 | 10/2010 | Larsson |
| 2010/0298791 A1 | 11/2010 | Jones et al. |

(56) References Cited

U.S. PATENT DOCUMENTS

| | | |
|---|---|---|
| 2011/0047766 A1 | 3/2011 | McAulay et al. |
| 2011/0071415 A1 | 3/2011 | Karwoski et al. |
| 2011/0092874 A1 | 4/2011 | Baschnagel |
| 2011/0130699 A1 | 6/2011 | Madsen et al. |
| 2011/0208102 A1 | 8/2011 | Chawki |
| 2011/0253303 A1 | 10/2011 | Miyachi et al. |
| 2012/0052230 A1 | 3/2012 | Olsson et al. |
| 2012/0220912 A1 | 8/2012 | Shang |
| 2012/0238933 A1 | 9/2012 | Murphy et al. |
| 2012/0277645 A1 | 11/2012 | Kikuta et al. |
| 2013/0012988 A1 | 1/2013 | Blume et al. |
| 2013/0041337 A1 | 2/2013 | Aali et al. |
| 2013/0066365 A1 | 3/2013 | Belson et al. |
| 2013/0084323 A1 | 4/2013 | Riebman et al. |
| 2013/0138068 A1 | 5/2013 | Hu et al. |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0282049 A1 | 10/2013 | Peterson et al. |
| 2013/0317405 A1 | 11/2013 | Ha et al. |
| 2014/0024989 A1 | 1/2014 | Ueda |
| 2014/0107561 A1 | 4/2014 | Dorian et al. |
| 2014/0121649 A1 | 5/2014 | Calco |
| 2014/0155916 A1 | 6/2014 | Hodgkinson et al. |
| 2014/0171888 A1 | 6/2014 | Croizat et al. |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott et al. |
| 2015/0257938 A1 | 9/2015 | Pensier |
| 2015/0297413 A1 | 10/2015 | Blanco |
| 2015/0314114 A1 | 11/2015 | La Rosa |
| 2015/0351767 A1 | 12/2015 | Zoll et al. |
| 2016/0030248 A1 | 2/2016 | Potters |
| 2016/0089145 A1 | 3/2016 | Quintero et al. |
| 2016/0296673 A1 | 10/2016 | Sambusseti |
| 2017/0035422 A1 | 2/2017 | Belson et al. |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |
| 2017/0273837 A1 | 9/2017 | Brueckner |
| 2017/0367806 A1 | 12/2017 | Gingras et al. |
| 2018/0085103 A1 | 3/2018 | Quintero et al. |
| 2018/0085259 A1 | 3/2018 | Quintero |
| 2018/0085260 A1 | 3/2018 | Quintero |
| 2019/0381207 A1 | 12/2019 | Jonn et al. |

FOREIGN PATENT DOCUMENTS

| | | |
|---|---|---|
| CN | 1697639 A | 11/2005 |
| CN | 201441532 U | 4/2010 |
| CN | 101965169 A | 2/2011 |
| CN | 102755216 A | 10/2012 |
| CN | 102781433 A | 11/2012 |
| CN | 203234898 A | 10/2013 |
| CN | 204766892 U | 11/2015 |
| EP | 0532275 A | 3/1993 |
| EP | 0730874 A | 9/1996 |
| EP | 0746293 A1 | 12/1996 |
| EP | 1161212 A | 8/2000 |
| EP | 2359782 A | 8/2011 |
| EP | 2377498 A | 10/2011 |
| EP | 2731563 A | 5/2014 |
| EP | 2531155 A | 10/2014 |
| EP | 2805698 A | 11/2014 |
| EP | 3574875 A1 | 12/2019 |
| GB | 2078763 A | 1/1982 |
| JP | 59-500046 A | 1/1984 |
| JP | 61-203020 A | 12/1986 |
| JP | 62-87624 A | 6/1987 |
| JP | 01-265967 A | 10/1988 |
| JP | 2-140948 A | 11/1990 |
| JP | 3-56429 U | 5/1991 |
| JP | 06-509966 A | 11/1994 |
| JP | 7-016258 A | 1/1995 |
| JP | 2001-265967 A | 9/2001 |
| JP | 1130927 S | 11/2001 |
| JP | 2002-512980 A | 5/2002 |
| JP | 2002-521139 A | 7/2002 |
| JP | 2002-537068 A | 11/2002 |
| JP | 2003-052741 A | 2/2003 |
| JP | 2003-153949 A | 5/2003 |
| JP | 58-124123 U | 1/2004 |
| JP | 2004-24905 A | 1/2004 |
| JP | 2006-061263 A | 3/2006 |
| JP | 2006-509966 A | 3/2006 |
| JP | 2007-522882 A | 8/2007 |
| JP | 3147394 U | 12/2008 |
| JP | 2009-022730 A | 2/2009 |
| JP | 1359502 S | 5/2009 |
| JP | 2011-004850 A | 1/2011 |
| JP | 1571238 S | 3/2017 |
| JP | 1629290 | 4/2019 |
| MX | 241113 A | 10/2006 |
| WO | WO 1983/002586 A | 8/1983 |
| WO | WO 1993/004650 A | 3/1993 |
| WO | WO 1995/004511 A | 2/1995 |
| WO | WO 1996/040797 A | 12/1996 |
| WO | WO 1998/026719 A | 6/1998 |
| WO | WO 2000/006213 A | 2/2000 |
| WO | WO 2000/049983 A | 8/2000 |
| WO | WO 2003/008002 A | 1/2003 |
| WO | WO 2004/049987 A | 6/2004 |
| WO | WO 2005/007020 A | 1/2005 |
| WO | WO 2005/051259 A | 6/2005 |
| WO | WO 2005/079674 A | 9/2005 |
| WO | WO 2006/017109 A | 2/2006 |
| WO | WO 2008/082444 A | 7/2008 |
| WO | WO 2009/067062 A | 5/2009 |
| WO | WO 2010/134873 A | 11/2010 |
| WO | WO 2011/152368 A | 12/2011 |
| WO | WO 2013/009725 A | 1/2013 |
| WO | WO 2014/083570 A | 6/2014 |
| WO | WO 2014/195710 A | 12/2014 |
| WO | WO 2015/135351 A | 9/2015 |

OTHER PUBLICATIONS

U.S. Appl. No. 10/887,884, filed Jul. 12, 2004, US-2006-0009099-A1, Abandoned.
U.S. Appl. No. 12/163,021, filed Jun. 27, 2008, US-2008-0255610-A1, U.S. Pat. No. 9,623,142, Apr. 18. 2017, Grant.
U.S. Appl. No. 12/207,984, filed Sep. 10, 2008, US-2009-00076542-A1, U.S. Pat. No. 9,655,622, May 23, 2017, Grant.
U.S. Appl. No. 14/864,033, filed Sep. 24, 2015, US2016-0089145, Abandoned.
U.S. Appl. No. 15/280,303, filed Sep. 29, 2016, US-2018-0085259, U.S. Pat. No. 10470934, Nov. 12, 2019, Grant.
U.S. Appl. No. 15/452,126, filed Mar. 7, 2017, US-2017-0173208, U.S. Pat. No. 10398800, Sep. 3, 2019, Grant.
U.S. Appl. No. 15/467,537, filed Mar. 23, 2017, US-2018-0271712, U.S. Pat. No. 10470935, Nov. 12, 2019, Grant.
U.S. Appl. No. 15/490,176, filed Apr. 18, 2017, US-2017-0216482, U.S. Pat. No. 10434211, Oct. 8, 2019, Grant.
U.S. Appl. No. 15/496,389, filed Apr. 25, 2017, US-2018-0303967, Publication.
U.S. Appl. No. 15/675,159, filed Aug. 11, 2017, US-2018-0085260, 10687986, filed Jun. 23, 2020, Grant.
U.S. Appl. No. 15/964,538, filed Apr. 27, 2018, US-2018-0243467, 10398802, Sep. 3, 2019, Grant.
U.S. Appl. No. 16/050,205, filed Jul. 31, 2018, 10993708, May 4, 2021, Grant.
U.S. Appl. No. 16/387,634, filed Apr. 18, 2019, US-2019-0240074, Publication.
U.S. Appl. No. 16/556,443, filed Aug. 30, 2019, US-2019-0381207, Publication.
U.S. Appl. No. 16/556,471, filed Aug. 30, 2019, US-2019-0381206, Publication.

(56) References Cited

OTHER PUBLICATIONS

U.S. Appl. No. 16/598,249, filed Oct. 10, 2019, US-2020-0038253, Publication.
U.S. Appl. No. 16/907,930, filed Jun. 22, 2020, US-2020-0315858, Publication.
U.S. Appl. No. 17/143,883, filed Jan. 7, 2021, US-2021-0121600, Publication.
U.S. Appl. No. 17/219,341, filed Mar. 31, 2021, US-2021-0212676, Publication.
U.S. Appl. No. 29/503,320, filed Sep. 25, 2014, U.S. Pat. No. D. 824,525, Jul. 31, 2018, Grant.
U.S. Appl. No. 29/613,662, filed Aug. 11, 2017, U.S. Pat. No. D. 848,624, May 14, 2019, Grant.
U.S. Appl. No. 29/635,782, filed Feb. 2, 2018, Abandoned.
U.S. Appl. No. 29/648,487, filed May 22, 2018, U.S. Pat. No. D. 854,171, Jul. 16, 2019, Grant.
U.S. Appl. No. 29/683,074, filed Mar. 11, 2019, U.S. Pat. No. D. 907,217, Grant.
U.S. Appl. No. 29/690,950, filed May 13, 2019, Filing.
U.S. Appl. No. 29/761,282, filed Dec. 8, 2020, Filing.
JP 7040744, 1995, English claims.
JP 3059327, 1991, English claims.
Japanese Office Action dated Feb. 19, 2019 for Design Appln. No. 2018-017274.
Japanese Office Action dated Feb. 26, 2019 for Patent Appln. No. 515463.
3M™ Steri-Strip Adhesive Closures Product Catalog Brochure, (2011) 4 pages.
3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al. Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery;* Apr. 1963; vol. 31; pp. 333-343.
Ashley et al.: Nonsutured closure of skin lacerations and nonsutured grafting of skin with a rapidly polymerizing adhesive; *Qtrly Bull.* Northwestern University (Evanston, III.) Medical School; 1962; vol. 36; pp. 189-194.
Brombeg et al.: Nonsuture fixation of split-thickness skin grafts; *Surgery,* Jun. 1964; vol. 55; pp. 846-853.
Cramer: Rapid Skin Grafting in Small Animals; *Plastic and Reconstructive Surgery and the Transplantation Bull;* Oct. 1962, vol. 30; pp. 149-150.
Cramer et al.: Autograft rejection induced by homografting. A phenomenon intermediate between homograft rejection and auto-immunity; *Plastic and Reconstructive Surgery;* Jun. 1965; vol. 35; pp. 572-587.
DeMaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).
INOU: Studies on the Surgical Use of Plastic Adhesive; *Am. Journal of Proctology;* 1962; vol. 13; pp. 219-226.
Jesse et al.: Fixation of split-thickness skin grafts with adhesive; *Plastic and Reconstructive Surgery;* Mar. 1964; vol. 33; pp. 272-277.
Kaplan: A technique of nonsuture wound closure with a plastic tissue adhesive; *Plastic and Reconstructive Surgery;* Feb. 1966; vol. 37(2); pp. 139-142.
Keddie et al.: Intrafollicular tinea versicolor demonstrated on monomer plastic strips; *Journal of Investigative Dermatology;* Sep. 1963; vol. 41; pp. 103-106.
Lazar, H.L. et al. 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
Pam Marketing Nut. Yikes! The Social Medica Quick Fix Band-Aids are Falling off! Jul. 2012 [earliest online date], [site visited May 8, 2018]. Available from Internet, ,URL: http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon;* Nov. 1964; vol. 30; pp. 753-755.
Raekallio et al.: Acute reaction to arterial adhesive in healing skin wounds; *Journal of Surgical Research;* Mar. 1964; vol. 4; pp. 124-127.
Stone: Nonsuture closure of cutaneous lacerations, skin grafting and bowel anastomosis; *American Surgeon;* Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M. et al. 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wang et al. 'Biodegradable microfluidic scaffolds for tissue engineering from amino alcohol-based poly(ester amide) elastomers' Organogenesis (2010) 6:4, pp. 212-216.
Wolfe et al.: The application of hydrostatic pressure to the burn injury, an experimental study: *Journal of Trauma: Injury Infections & critical Care;* May 1962; vol. 2; pp. 262-272.
ZipLine medical Zip Surgical Skin Closure Brochure (2013) 4 pages.
Corrected International Search Report International Application No. PCT/US2005/004948 dated Jun. 22, 2005.
Extended European Search Report re: 14166813.7 dated Jul. 7, 2014.
International Preliminary Report on Patentability for International Application No. PCT/US2005/024042 dated Jan. 16, 2007.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
Written Opinion re: PCT/US2015/051919 dated Apr. 14, 2016.

(56) References Cited

OTHER PUBLICATIONS

Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.
N/A, "Scar nose & Rinoplasty Surgery—New Gel+Demo:Nose Silicone Gel Sheet (beige)www newgelplus.com", www.youtube.com, 2012, pp. 1-3, Page Number.
N/A, "Silagen Silicone Sheeting Strips Review|the skin spot", www.youtube.com, 2017, pp. 1-3, Page Number.

\* cited by examiner

ADHESIVE-CONTAINING WOUND CLOSURE DEVICE AND METHOD

BACKGROUND OF THE INVENTION

1. Field of Invention

The present invention relates to medical and surgical wound closure and management, and methods for making and using such devices. In particular, the present invention relates to medical and surgical wound closure and management, and related methods, where the device incorporates a polymerizable adhesive material. The materials and methods of the present invention provide an improvement over, and a substitute for, conventional bandages, sutures and staples, and provide improved methods for both approximating and covering wounds, thus providing improved wound management.

2. Description of Related Art

There are currently in primary use at least four basic ways for closing wounds resulting from surgical incisions or accidental lacerations. These are sutures, surgical staples, surgical skin tapes, and adhesive compositions. Sutures are generally recognized as providing adequate wound support for the duration of wound healing. However, suturing involves additional trauma to the wound, as the needle and suture material must be passed through the tissue at the margins of the wound. In addition, suturing can cause cosmetically unattractive wound closure marks, can be time consuming, and, depending on techniques and types of sutures used, may require removal. Such removal entails further medical attention and can involve additional pain and trauma to the patient particularly if the sutures become embedded in the wound.

Surgical staples have disadvantages similar to sutures in terms of cosmetic result. Further, removal of the staples can be painful and, depending on location and patient pain threshold, may require topical anesthetics.

Skin closure strips, such as conventional adhesive bandages, are utilized for closure of relatively superficial skin wounds. However, the contact adhesives that are used with such strips typically retain holding power for no more than a day or two and can lose holding power quickly in the presence of moisture, for example, perspiration.

Direct application of adhesives has also been proposed and used for wound closure purposes, especially involving cyanoacrylate adhesives. Such materials are achieving more widespread use for wound closure.

For example, monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and staples in wound closure as well as for covering and protecting surface wounds such as lacerations, abrasions, burns, stomatitis, sores, and other surface wounds. When an adhesive is applied, it is usually applied in its monomeric form, and the resultant polymerization gives rise to the desired adhesive bond.

For example, polymerizable 1,1-disubstituted ethylene monomers, and adhesive compositions comprising such monomers, are disclosed in U.S. Pat. No. 5,328,687 to Leung et al. Suitable methods for applying such compositions to substrates, and particularly in medical applications, are described in, for example, U.S. Pat. Nos. 5,582,834, 5,575,997, and 5,624,669, all to Leung et al.

Combinations of the above approaches have also been used in the art. For example, attempts have been made to combine the use of sutures or stapes and adhesive compositions. See, for example, U.S. Pat. No. 5,254,132. Likewise, attempts have been made to combine the use of conventional bandages or tapes and adhesive compositions. See, for example, U.S. Pat. Nos. 5,259,835 and 5,445,597. However, these approaches have typically met the same issues as described above for the individual approaches, namely difficulties arising from the use of the sutures, staples and/or bandages or tapes.

Accordingly, a need continues to exist for improved materials and methods for wound approximation. A need also continues to exist for improved materials and methods that have a wider range of applications, from external to internal use, and from essentially non-biodegradable (where the materials are removed from the application site) to biodegradable (where the materials are not directly removed from the application site, but instead degrade over time).

SUMMARY OF THE INVENTION

The present invention addresses the above needs in the art, and others, by providing improved materials and methods for wound approximation.

In embodiments, the materials and methods of the present invention provide significant advantages over the current materials and methods for wound closure. The materials and methods of the present invention can fully replace the use of bandages, sutures, and/or staples on a variety of wounds and tissue surfaces, thereby providing not only improved wound approximation, but also improved wound closure. These advantages include, among others, improved wound closure, provision of an improved durable microbial barrier, reduced procedure time, improved cosmesis, less pain (during staple/suture removal) resulting in increased patient satisfaction, and improved financial/economic outcomes by eliminating follow-up visits for staple/suture removal.

In an embodiment, the present invention provides a tissue bonding article, comprising:

a flexible or compliant material;

an adhesive substance applied over at least a portion of a bottom side of said flexible or compliant material; and a polymerizable adhesive composition permeated throughout said flexible or compliant material.

In a modification of the above embodiment, the tissue bonding article can further include a polymerization initiator or rate modifier, a bioactive material, or combinations thereof. Such additive can be included, for example, as part of the flexible or compliant material, or mixed with the polymerizable adhesive composition.

In another embodiment, the present invention provides a method of bonding tissue, comprising:

placing a flexible or compliant substrate over a section of tissue;

applying a polymerizable adhesive composition over and substantially covering the flexible or compliant substrate; and allowing the polymerizable adhesive composition to permeate into and under the flexible or compliant substrate and polymerize to form a composite structure bonded to said tissue.

As with the tissue bonding article described above, the method of bonding tissue according to the present invention can also incorporate a polymerization initiator or rate modifier, a bioactive material, or combinations thereof. Such additive can be included, for example, as part of the flexible or compliant material, or mixed with the polymerizable adhesive composition.

In other embodiments of the present invention, the flexible substrate can include one or more adhesive strips, which carry the adhesive substance and thereby adhere the flexible substrate to the desired application site.

BRIEF DESCRIPTION OF THE DRAWINGS

These and other advantages and features of this invention will be apparent from the following, especially when considered with the accompanying drawings, in which:

FIG. 7b is a perspective view of a different embodiment of the present invention shown in FIG. 7a.

DETAILED DESCRIPTION OF PREFERRED EMBODIMENTS

Figure 1:
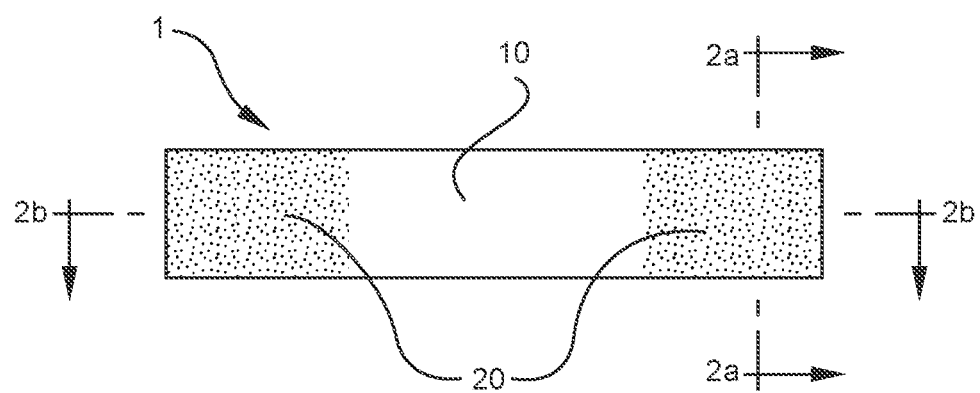
FIG. 1 is a schematic view of a first embodiment of the present invention.
Figure 2A:
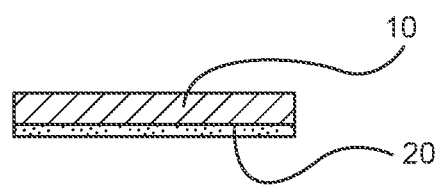
FIGS. 2a and 2b are cross-sectional views of the embodiment of FIG. 1.
Figure 2B:
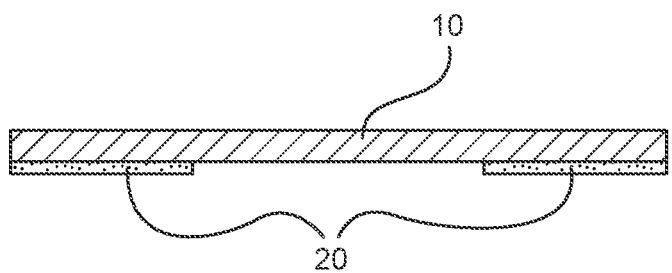

An embodiment of the present invention is shown schematically in FIG. 1. In FIG. 1, a flexible substrate 1 is shown as including a flexible material 10 coated on several portions with an adhesive substance 2. FIGS. 2a and 2b are cross-sectional views of the flexible substrate 1 of FIG. 1, taken along lines 2a-2a and 2b-2b, respectively. FIGS. 1 and 2a-2b show that, in embodiments, the adhesive substance does not cover an entire portion of the flexible substrate, but only portions thereof.

In the embodiment of FIG. 1, the flexible or compliant material 10 can be formed of any suitable flexible or compliant material, providing that the aims of the present invention are obtained. Preferably, the flexible or compliant material 10 is a material that is flexible, porous, and non-toxic. As used herein, the term "flexible" is used to refer to the flexible or compliant material 10. However, unless stated differently in context, the term "flexible" is meant to cover a range of materials, which exhibit one or more properties such as being flexible, compliant, elastic, or memory retentive. For example, "flexible" is also meant to refer to materials that exhibits elastic or memory properties, i.e., the ability for the material to return to its original shape when stresses applied thereto are reduced or eliminated.

The flexible material is preferably flexible or compliant, to allow the flexible substrate to be placed on the desired surface (such as skin, organ, tissue, or the like) in a manner that allows the flexible substrate to conform to the topology of the desired surface. Likewise, the flexible material is preferably porous, to allow the subsequently applied polymerizable adhesive material to pass through or permeate through the flexible material and to polymerize as a layer beneath the flexible material, while adhering the flexible material to the desired substrate. Such porosity will also preferably allow air and water to pass through the flexible material. Depending upon the degree of porosity (and/or the size of the openings in the mesh), such porosity of the flexible material or ability of air and water to permeate through the flexible material may be tailored to either remain after the final composite material is formed, or to be absent therefrom. The flexible material is also preferably non-toxic, as it is intended to be used as a wound covering, such as on biological tissues. As such, the flexible material should be biologically compatible with the desired substrate (such as tissue, skin, organ, or the like), and is preferably a material that is governmentally approved or generally regarded as safe for the desired purpose.

In other embodiments, the flexible material may be selected to be elastic or have some memory effect. In such embodiments, the elastic properties of the flexible material may desirably provide a degree of pressure or stress at the application site, for example, to maintain wound edge approximation. Likewise, in embodiments where such additional degree of pressure or stress at the application site is not desired, the flexible material may be selected to have less or no elasticity.

In embodiments of the present invention, the flexible material can be either biodegradable, or not biodegradable. By "biodegradable" in this invention is meant that the flexible substrate biodegrades over time in vivo, such that it does not require physical removal of the composite structure after a set period of time. Thus, for example, a biodegradable flexible material is one that, in the in vivo environment, will biodegrade over a period of from about one week to about five years. A non biodegradable material is one that does not biodegrade in an in vivo environment within about five years. Such a non biodegradable material thus would require physical removal of the composite structure at a desired time, rather than slowly deteriorating over time. Likewise, in some embodiments, it is preferred that the combination of materials forming the composite structure (i.e., the flexible material and the polymerizable adhesive composition) together be biodegradable, while in other embodiments, it is preferred that the combination of materials forming the composite structure (i.e., the flexible material and the polymerizable adhesive composition) together be not biodegradable. Biodegradable and non-biodegradable polymerizable adhesive compositions are known in the art and are described below. Alternatively, combination of two or more biodegradable and/or non-biodegradable materials can be used, to provide tailored results in terms of properties such as biodegradation and the like.

For biodegradable materials, a range of materials can be selected as the flexible material, preferably to provide a desired target biodegradation time. Thus, for example, suitable materials can be selected to provide either a short biodegradation period (such as between about one week and about two months) or a longer biodegradation period (such as between about two months and about five years). Suitable selection of the flexible material will thus allow tailoring of the flexible substrate to the particular application. For example, in embodiments where the flexible substrate is used to form a composite structure on the surface of a patient's skin (such as in the conventional context of a bandage), it is desirable that the flexible substrate is not biodegradable. Rather, after a set period of time, the composite structure is physically removed, either to permit completion of healing or to reapply a new composite structure. In other embodiments, however, it may be desirable that the composite structure biodegrade over a set period of time, for example when the composite structure is used internally where subsequent removal would otherwise require further trauma to the tissue.

In embodiments, it is preferred that the flexible material is a mesh material. Suitable mesh materials can be formed of either synthetic or natural materials. Such mesh material can be formed of either woven or non-woven fabrics or materials. The flexible material may be, for example, any suitable polymeric film, plastic foam (including open celled foam), a woven fabric, knitted fabric, a non-woven fabric, mixture thereof, or the like. In particular, suitable flexible materials may thus be prepared, for example, from nylon, a polyolefin film, such as polyethylene, polypropylene, ethylene propylene copolymers, and ethylene butylene copolymers, polyurethanes, polyurethane foams, polystyrenes, plasticized polyvinylchlorides, polyesters, polyamides, and cotton. Suitable specific examples include, for example, nylon, polyethylene, polypropylene, ethylene propylene copolymers, ethylene butylene copolymers, polyurethane, polystyrene, plasticized polyvinylchloride, polyester, polyamide, cotton, polytetrafluoroethylene (PTFE), biovascular material, collagen, Gore-Tex®, Dacron™, etc.

In some embodiments, it is preferred that the mesh material not be formed of elastin, or elastin-based materials. Although elastin may be suitable for some uses, synthetic materials are preferred in embodiments in view of their availability, ease of manufacture, physical properties such as strength and durability, and biological compatibility. Thus, in such embodiments, it is preferred that the mesh material is substantially or completely free of elastin or elastin-based materials. Further, in such embodiments, it is preferred that the entire flexible substrate (i.e., the combination of the flexible material and the adhesive substance) is substantially or completely free of elastin or elastin-based materials.

In other embodiments, it is preferred that the flexible material be formed of a synthetic, semi-synthetic, or natural organic material. Thus, for example, it is preferred that the flexible material be formed of a synthetic or natural polymer material, but not from a material such as metal (such as silver, steel or the like) or glass or ceramic.

The flexible material is preferably flexible, as described above, yet resistant to tearing. In one embodiment, the thickness of the flexible material of the present invention is from about 0.1 mil to about 50 mils. In another embodiment, the thickness of the flexible material is from about 0.5 mil to about 20, preferably from about 0.7 mil to about 10 mils, or from about 1 mil to about 5 mils.

The flexible material may be opaque or translucent. In some embodiments of the present invention, the flexible material is provided to have a skin color, such that the flexible material masks the appearance of the underlying surface (such as a wound). However, in other embodiments, the flexible material can be provided with "designer" colors and/or patterns, or even cartoon character designs. In other embodiments, the flexible material may be clear, thus not masking the underlying surface.

Figure 3:
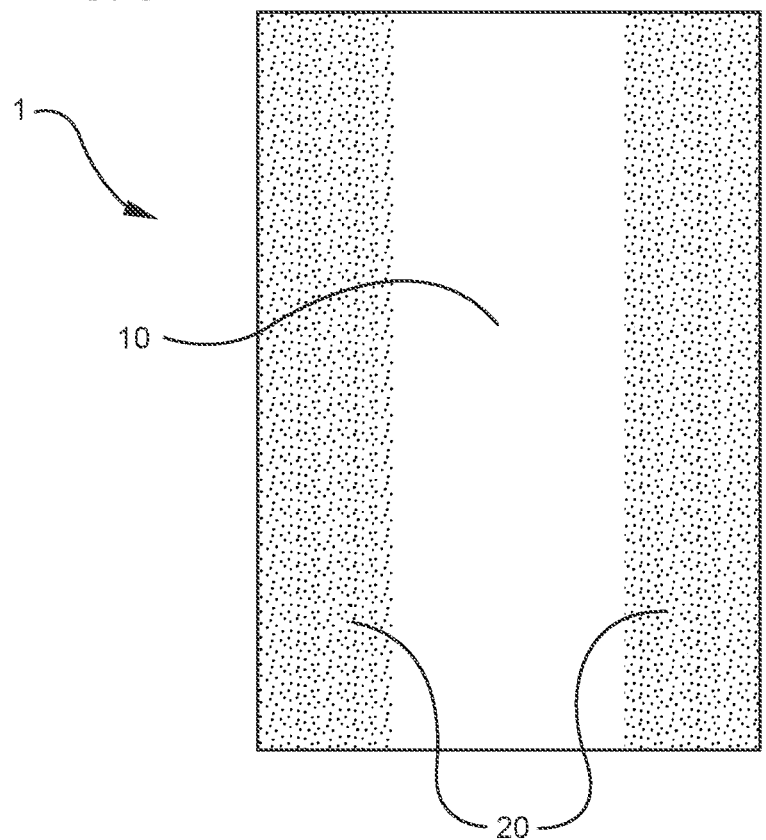
FIG. 3 is a schematic view of another embodiment of the present invention.

As shown in FIGS. 1-3, the flexible substrate 1 includes an adhesive substance 20 applied to portions of the flexible material 10. Preferably, as shown in FIG. 1, the adhesive substance 20 is applied to the flexible material 10 on opposite ends of the flexible material 10. In this manner, the flexible substrate 1 can be applied over a wound or other desired substrate such that the portion of the flexible material not coated with the adhesive substance straddles the wound. (This use of the composite structure will be described in more detail below.) Accordingly, the adhesive substance is applied to the same side of the flexible material, and the exposed adhesive substance can be covered by a suitable release layer or liner (not shown) to preserve the adhesiveness of the flexible substrate until time of use.

Figure 4:
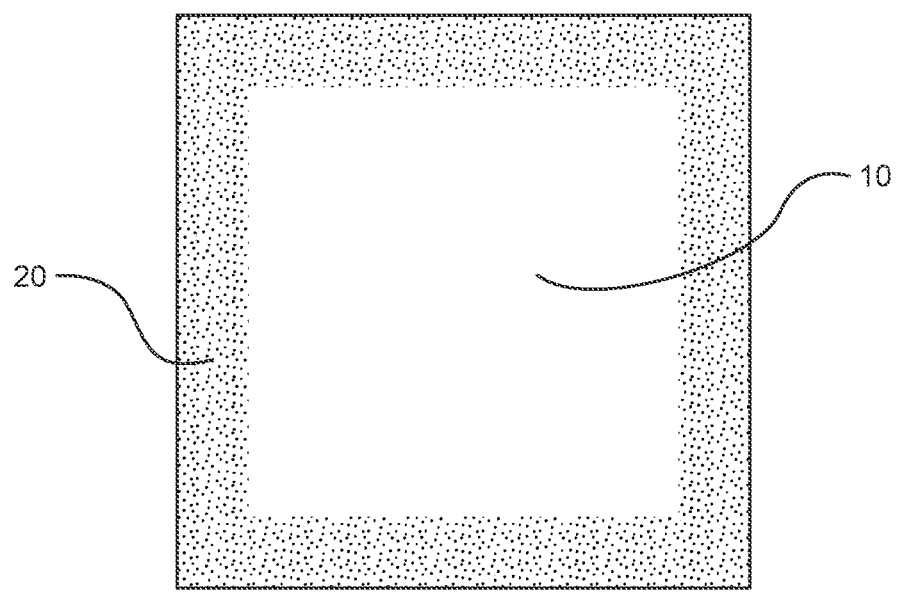
FIG. 4 is a schematic view of another embodiment of the present invention.
Figure 5:
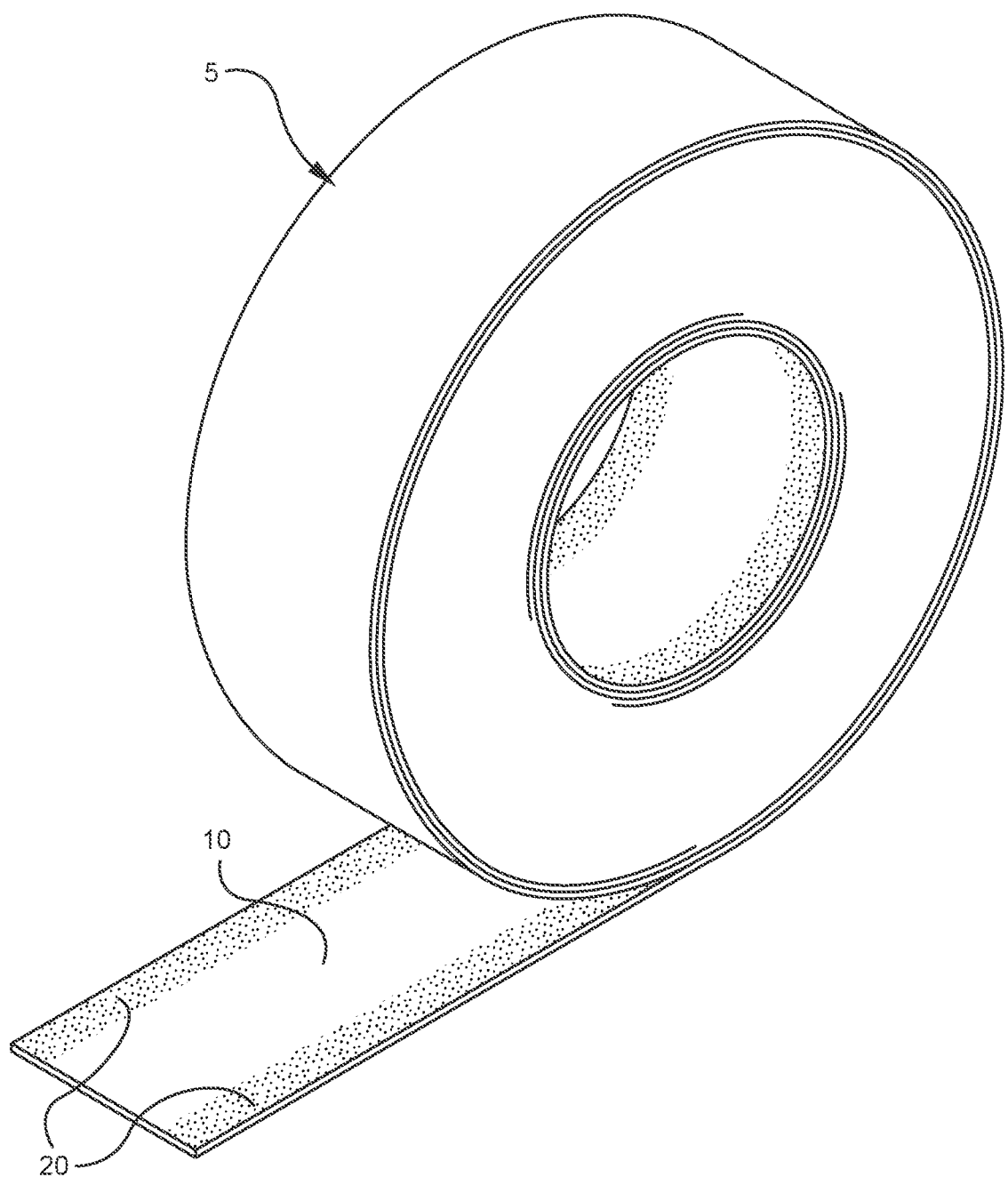
FIG. 5 is a schematic view of another embodiment of the present invention.

Although not limited to any particular orientation, the adhesive substance can be applied either on a short or a long edge of the flexible material 10. Thus, for example, FIG. 1 shows the adhesive substance 20 applied on opposite short (substantially parallel) ends of a rectangular flexible material 10. This embodiment roughly corresponds to a conventional bandage, where the adhesive portions are applied on opposite sides of a wound and the central (uncoated) portion of the flexible material covers the wound. Alternatively, FIG. 3 shows an embodiment where the adhesive substance 20 is applied on opposite long (substantially parallel) ends of a rectangular flexible material 10. This embodiment roughly corresponds to a tape design, where the edges of the tape are applied on opposite sides of a lengthwise wound and the central (uncoated) portion of the flexible material covers the lengthwise wound. Of course, the invention is not limited to such embodiments, and other orientations of the invention will be readily apparent to those skilled in the art based on the present disclosure. For example, FIG. 4 shows an embodiment where the adhesive substance 20 is applied on all four ends or edges of a square flexible material 10, and FIG. 5 shows an embodiment where the flexible substrate is in a form of a roll of material 5, and the adhesive substance 20 is applied on the long lengthwise edges of the flexible material 10.

Preferably, the adhesive substance is thus applied to the flexible material so as to form distinct first, second and third regions across a width or length dimension of the flexible material. In the first region, the flexible substrate is not covered with the adhesive substance. This region is intended to be placed over an underlying wound or tissue trauma, such that the wound is not contacted (or is substantially not contacted) by the adhesive substance. The second and third regions, which adjoin the first region on opposing edges thereof, are the regions where the adhesive substance is applied. These second and third regions are intended to be placed on opposite sides of an underlying wound or tissue trauma, to temporarily secure the flexible substrate to the desired application site, such that the wound per se is not contacted (or is substantially not contacted) by the adhesive substance.

Although not specifically shown in the figures, a suitable backing or release material may also be used to cover the adhesive substances applied to the bottom side of the flexible material. Such backing materials are well known in the art for covering pressure sensitive adhesives and can include, for example, paper, plastic, or the like.

When forming rectangular flexible substrates for use in the present invention, any suitable dimensions of the material can be provided. For example, in the conventional bandage configuration, where the adhesive substance is provided on the short parallel ends of the flexible material, the flexible material can range in width from about ¼ inch to about 2 or 3 inches or more, although preferred widths in embodiments may be from about ½ to about 1 or 1½ inches, and can range in length from about ½ inch to about 4 or 5 inches or more, although preferred lengths in embodiments may be from about 1 to about 2 or 3 inches. Likewise, in the configuration of being a lengthwise bandage or rolled tape, where the adhesive substance is provided on the long parallel ends of the flexible material, the flexible material can range in width from about ½ inch to about 4 or 5 inches or more, although preferred widths in embodiments may be from about 1 to about 2 or 3 inches, and can range in length from about 1 inch to about 6 or 8 inches or more, although preferred lengths in embodiments may be from about 2 to about 4 or 5 inches. However, a particular advantage of this embodiment is that the flexible substrate may be used to form a composite structure over a longer wound, such as a long laceration on incision. As such, embodiments of the present invention can provide a flexible substrate having length exceeding 8 or even 12 inches, such as ranging in lengths up to 18 inches, 24 inches, 30 inches, or more. When provided in the configuration of a roll, the flexible substrate can have virtually any practical length, such as 5, 6, 8, 10, or 12 feet or more, which can be cut to desired length at the time of use. Of course, it will be apparent that the materials of the present invention are not limited to ant particular dimensions, and that the dimensions (length, width, thickness, etc.) of the flexible substrate can be varied and tailored, as desired.

As such, various sized flexible materials can be prepared and packaged for use. For example, shorter length materials (for example, 15-inch) can be prepared and packaged for use in "short laceration" applications, while longer length materials (for example, 30-inch) can be prepared and packaged for use in "long laceration" applications. In other embodiments, a variety of length materials can be provided, with the intention that the materials are single use materials, where any leftover length of the flexible material is discarded. Such single-use embodiments are particularly desirable where the flexible material is sterilized, and sterility is desired to be maintained until the time of use. In other embodiments, such as where sterility is not a requirement, a longer length of flexible material can be provided where any unused portion can be saved for later use.

Still other configurations for the flexible substrate 1 will be apparent to those skilled in the art. For example, although described above as being in rectangular or square configurations, the flexible substrate can take any number of other shapes, which can be designed for particular applications. For example, circular or round flexible materials can be used, such as to cover blister bases, sores, or the like; arc-shaped (curved rectangular shaped) flexible materials can be used, such as to cover curved lacerations or incisions; and the like. Other shapes, such as oval, triangular, polygonal, semi-circular, and the like, can also be used, in embodiments.

Although shown in the figures as dotted areas, the adhesive substance, preferably with a release layer or backing when the material is not to be immediately used, may be applied to the desired portions of the flexible material in either a continuous or discontinuous manner. Thus, for example, the adhesive substance can be applied as a solid layer over the desired area, or in a set or random pattern. Preferably, the adhesive substance is applied to form a pattern on the flexible material. The adhesive may be applied in any number of patterns, including, for example, in a sine wave using either a smooth pattern (rounded waves) or a sharp pattern (triangle shaped waves) closely packed together. In a preferred embodiment, the adhesive forms a continuous network so that the adhesive-free areas are not interconnected. The adhesive substance is typically present in coat weight from about 10 to about 200, or from about 20 to 150 grams per square meter (gsm). Of course, other coat weights of the adhesive substance can be used, as desired.

The adhesive substance used in the flexible substrate of the present invention may, for example, be any suitable adhesive substance. Preferably, the adhesive substance is a medical grade adhesive, such as acrylic based pressure sensitive adhesives (PSAs), rubber based pressure sensitive adhesives, silicone pressure sensitive adhesives, mixtures thereof, or the like. In embodiments, it is preferred that the adhesive substance be different from the polymerizable adhesive composition. Thus, for example, it is preferred that while the polymerizable adhesive composition can be, for example, a polymerizable monomeric adhesive composition, the adhesive substances is an adhesive material that is not a polymerizable adhesive composition, such as a pressure sensitive adhesive.

Suitable rubber based PSAs include, but are not limited to, those taught in U.S. Pat. No. 5,705,551 and in U.S. Pat. No. 4,080,348, the disclosures of which are hereby incorporated by reference. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

A particularly useful rubber based adhesive is that which has a thermoplastic elastomeric component and a resin component. The thermoplastic elastomeric component contains about 55-85 parts of a simple A-B block copolymer wherein the A-blocks are derived from styrene homologs and the B-blocks are derived from isoprene, and about 15-45 parts of a linear or radical A-B-A block copolymer wherein the A-blocks are derived from styrene or styrene homologs and the B-blocks are derived from conjugated dienes or lower alkenes, the A-blocks in the A-B block copolymer constituting about 10-18 percent by weight of the A-B copolymer and the total A-B and A-B-A copolymers containing about 20 percent or less styrene. The resin component consists of essentially of tackifier resins for the elastomeric component. In general any compatible conventional tackifier resin or mixture of such resins may be used. These include hydrocarbon resins, rosin and rosin derivatives, polyterpenes and other tackifiers. The adhesive composition contains about 20-300 parts of the resin component per one hundred parts by weight of the thermoplastic elastomeric component. One such rubber based adhesive is commercially available from Ato Findley under the trade name HM3210.

Useful acrylic based PSAs include, but are not limited to, those taught in U.S. Pat. Nos. 5,947,917 and 5,164,444 (acrylic emulsion), U.S. Pat. No. 5,623,011 (tackified acrylic emulsion). It can also be radiation curable mixture of monomers with initiators and other ingredients such as those taught in U.S. Pat. No. 5,232,958 (UV cured acrylic) and U.S. Pat. No. 5,232,958 (EB cured). The disclosures of these patents are hereby incorporated by reference.

It is contemplated that any acrylic based polymer capable of forming an adhesive layer with sufficient tack to adhere to the flexible material, the release liner or to a substrate, and with acceptable adhesion to skin, may function in the present invention. In certain embodiments, the acrylic polymers for the pressure-sensitive adhesive layers include those formed from polymerization of at least one alkyl acrylate monomer or methacrylate, an unsaturated carboxylic acid and optionally a vinyl lactam. Examples of suitable alkyl acrylate or methacrylate esters include, but are not limited to, butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and the like, and mixtures thereof. Examples of suitable ethylenically unsaturated carboxylic acids include, but are not limited to, acrylic acid, methacrylic acid, fumaric acid, itaconic acid, and the like, and mixtures thereof. A preferred ethylenically unsaturated carboxylic acid monomer is acrylic acid. Examples of suitable vinyl lactams include, but are not limited to, N-vinyl caprolactam, 1-vinyl-2-piperidone, 1-vinyl-5-methyl-2-pyrrolidone, vinyl pyrrolidone, and the like, and mixtures thereof.

The adhesive substance may also include a tackifier. Tackifiers, are generally hydrocarbon resins, wood resins, rosins, rosin derivatives, and the like. It is contemplated that any tackifier known by those of skill in the art to be compatible with elastomeric polymer compositions may be used with the present embodiment of the invention. One such tackifier, found to be useful is Wingtak 10, a synthetic polyterpene resin that is liquid at room temperature, and sold by the Goodyear Tire and Rubber Company of Akron, Ohio. Wingtak 95 is a synthetic tackifier resin also available from Goodyear that comprises predominantly a polymer derived from piperylene and isoprene. Other suitable tackifying additives may include Escorez 1310, an aliphatic hydrocarbon resin, and Escorez 2596, a $C_5$-$C_9$ (aromatic modified aliphatic) resin, both manufactured by Exxon of Irving, Tex. Of course, as can be appreciated by those of skill in the art, a variety of different tackifying additives may be used to practice the present invention.

In addition to the tackifiers other additions may be included in the adhesive substances to impart desired properties. For example, plasticizers may be included and they are known to decrease the glass transition temperature of an adhesive composition containing elastomeric polymers. Shellflex 371 plasticizer is an example of a useful naphthenic processing oil available from Shell Oil Company of Houston, Tex. Antioxidants also may be included on the adhesive substance. Also included as suitable are Irgafos 168 antioxidant and Irganox 565 antioxidant available from Ciba-Geigy, Hawthorne, N.Y. Cutting agents such as waxes and surfactants also may be included in the adhesive substance.

Other optional materials that may be added to the adhesive substance layer in minor amounts (typically less than about 25% by weight of the elastomeric phase) include pH controllers, medicaments, bactericides, growth factors, wound healing components such as collagen, antioxidants, deodorants, perfumes, antimicrobials and fungicides.

Useful silicone pressure sensitive adhesives include those commercially available from Dow Corning Corp., Medical Products and those available from General Electric. Examples of silicone adhesives available from Dow Corning include those sold under the trademarks BIO-PSA X7-3027, BIO-PSA X7-4919, BIO-PSA X7-2685, BIO-PSA X7-3122 and BIO-PSA X7-4502. Additional examples of silicone pressure sensitive adhesives useful in the present invention are described in U.S. Pat. Nos. 4,591,622, 4,584,355, 4,585, 836 and 4,655,767, the entire disclosures of which are incorporated herein by reference.

In another embodiment of the present invention, the flexible substrate can be coated on one side with an adhesive substance. In this embodiment, the adhesive substance can be located on substantially an entire surface of the flexible substrate, rather than only on opposing edges of the flexible substrate as described above. When prepared in this manner, the adhesive substance can be coated to cover the entire surface in a continuous coating or layer. Alternatively, or preferably in some embodiments, the coating is discontinuous to provide areas that are not covered by the adhesive substance, such as by the adhesive substance being provided in a form of regular or random spots, lines, or the like. Where the adhesive substance does not cover the entire surface of the flexible substrate to form a continuous layer, it is preferred that the adhesive is coated on at least 25% but no more than 75% of the surface area, and more preferably between about 40 and about 60% of the surface area.

In this embodiment, the flexible substrate can be applied to the desired surface much in the same manner as a piece of tape, where substantially the entire surface of the flexible substrate adheres to the desired surface. The polymerizable adhesive composition can then be applied to the exposed surface of the flexible substrate, in the manner as described above. A benefit of this embodiment is that the entire applied flexible substrate can be retained on the desired surface, without trimming off the adhered portions in the manner described above.

When the flexible substrate is provided according to this embodiment, it is preferred that the adhesive substance applied to the surface of the flexible substrate be a pressure sensitive adhesive, which preferably exhibits a low degree of adhesiveness. The adhesive substance to be applied can be, if desired, the same as the adhesive substance described above, which is applied to only portions of the flexible substrate. Or, the adhesive substance used in this embodiment can be a weaker or different adhesive substance. That is, the purpose of the adhesive substance is only to maintain the flexible substrate in position on the desired surface, and optionally provide a minimal adhesion force to approximate or appose the wound surfaces, until the polymerizable adhesive composition is applied and allowed to set to fully adhere the flexible substrate to the desired surface. The adhesive substance is thus weak enough to allow the applied polymerizable adhesive material to penetrate through the flexible substrate and the applied adhesive substance, to form a polymerized bond between the flexible substrate (and applied adhesive substance) and the underlying desired substrate.

In this embodiment, any suitable adhesive substance can be used, as desired. Preferably, the adhesive substance should be non-toxic, and capable and/or approved for use on biological surfaces. Suitable adhesive substances thus include, for example, those adhesive substances commonly used in production of conventional adhesive bandages. Furthermore, in this embodiment where the adhesive substances covers substantially an entire face of the flexible material, and thus remains in the final composite structure, it is preferred that the polymerizable adhesive composition (described in more detail below) be able to interact with and/or solubilize the adhesive substances. That is, it is preferred that the polymerizable adhesive composition be able to in essence replace the adhesive substance as the primary means of attaching the composite structure to the underlying substrate (application site, such as tissue or wound). This can occur, for example, either by the polymerizable adhesive composition solubilizing the adhesive substance, or by the polymerizable adhesive composition being able to bond the flexible material to the underlying substrate through gaps or voids either pre-existing or created in the adhesive substance layer.

Preferably, the adhesive substances is the only attachment means present on the flexible substrate for attaching the flexible material to the desired application or treatment site. Thus, for example, the flexible substrate does not further include other physical attachment means such as hooks, barbs, pins, projections, or the like, which operate to physically latch or otherwise attach the flexible substrate to the desired application or treatment site. Such attachment means are not desired, for example, because they introduce additional trauma to the underlying surface. Thus, it is preferred that the flexible substrate not include features that penetrate even surface layers of the underlying substrate, such as dermal layers of the skin.

In addition to including the flexible material and an amount of adhesive substance, as described above, the flexible substrate can, if desired, include one or more chemical materials located within the flexible material. For example, one or more chemical substances can be dispersed in the flexible material, such as being chemically bound, physically bound, absorbed, or adsorbed to the flexible material. Thus, for example, the flexible substrate can include a polymerization initiator or rate modifier, or can include one or more bioactive materials. As desired, the one or more chemical substances can be either immobilized on the flexible material, for example so that it has a desired effect but is not detached from the flexible material during use, or it can be attached to the flexible material in a manner such that it becomes detached during use.

For example, it may be desirable to immobilize a polymerization initiator or rate modifier on the flexible material, so that the initiator or rate modifier provides the desired initiation or rate modification effect to a subsequently applied polymerizable adhesive composition, but without the initiator or rate modifier becoming detached from the flexible material and its residues dispersed in the resultant polymeric material. Alternatively, for example, a bioactive material may be initially attached to the flexible material, but only in such a manner that it becomes mobilized or solubilized by a subsequently applied polymerizable adhesive composition and dispersed in the resultant polymeric material.

If desired, a combination of chemical substances can also be provided on the flexible material, to provide multiple effects. For example, as described above, a first chemical species (such as a polymerization initiator or rate modifier) can be immobilized on the flexible material, while a second, different chemical species (such as a bioactive material) can be detachably attached to the flexible material. Other combinations of chemical species and resultant effects are also envisioned by the present invention.

When present in or on the flexible material, the chemical substances (i.e., polymerization initiator, rate modifier, and/ or bioactive materials, or other additives), can be incorporated in or on the flexible material in any suitable manner. For example, the chemical substance can be added to the flexible material by contacting the flexible material with a solution, mixture, or the like including the chemical substances. Alternatively, the chemical substance can be incorporated into or onto the flexible material during manufacture of the flexible material, such as during molding or the like of the flexible material.

A method for using the flexible substrate and resultant composite structure will now be described.

The materials of the present invention are advantageously used as wound dressings. For example, the materials of the present invention are advantageously used as replacements for conventional bandages, or as replacements for conventional use of sutures and staples for closing wounds. As compared to conventional bandages, the flexible substrate of the present invention generally provides the same wound approximation and pressure benefits. However, because the flexible substrate is used to provide a composite structure by the addition of a polymerizable adhesive composition, the resultant composite structure provides significant benefits over the conventional bandage in terms of improved wound management, stronger adhesion to the underlying application site, microbial barrier properties, improved patient satisfaction, and the like. Thus, for example, the materials of the present invention, by means of the applied adhesive substance on the bottom side of the flexible material, provide wound approximation prior to application of a polymerizable adhesive material to the upper surface of the flexible material, which subsequently permeates through the flexible material as the adhesive polymerizes, to form a flexible, adherent wound dressing. The portions of the flexible material previously coated with the adhesive substance can then, if desired, be trimmed away to provide a unitary composite structure over the wound. Furthermore, as compared to conventional sutures and staples, the composite structure of the present invention also generally provides the same wound approximation and pressure benefits. However, because the composite structure uses a polymerizable adhesive composition rather than punctures for adhesion to the underlying application site, the resultant composite structure provides significant benefits over the conventional sutures and staples in terms of improved wound management, stronger adhesion to the underlying application site, microbial barrier properties, improved patient satisfaction, less tissue trauma (since additional punctures are not made), lessened scarring, and the like.

One method according to the present invention is shown successively in FIGS. 6a-6e. Although the method is shown using a flexible substrate such as that shown in FIG. 3 or FIG. 5, the invention is not limited to this embodiment. In FIGS. 6a-6e, a surface is shown having a lengthwise wound. Thus, for example, the figures show a skin surface (arm or leg 30) having a jagged, lengthwise wound or laceration 40. The wound is closed using the composite structure according to the present invention.

Figure 6A:
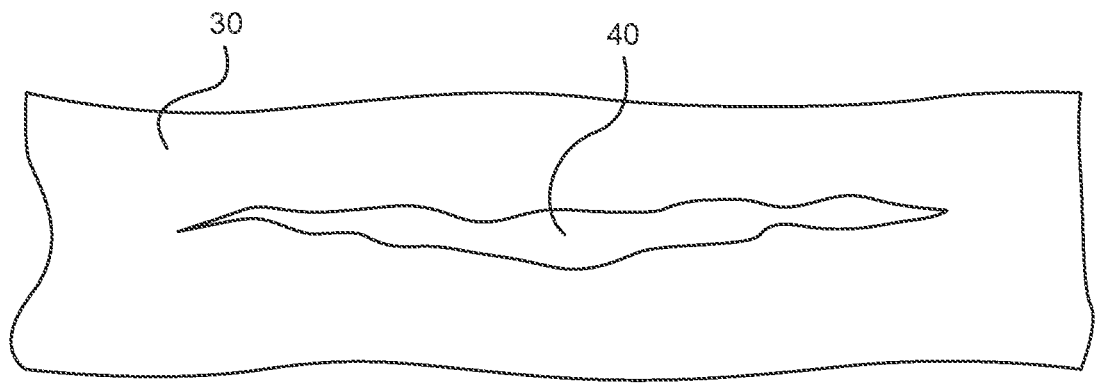
FIGS. 6a-6e illustrate a method of using a composite structure according to an embodiment of the present invention.

In a first step as shown in FIG. 6a, the arm or leg 30 is shown having an open wound 40. Preferably, the wound is first cleaned by removing excess exudates (blood or the like) to provide as dry a wound as possible to assist in wound closure.

Figure 6B:
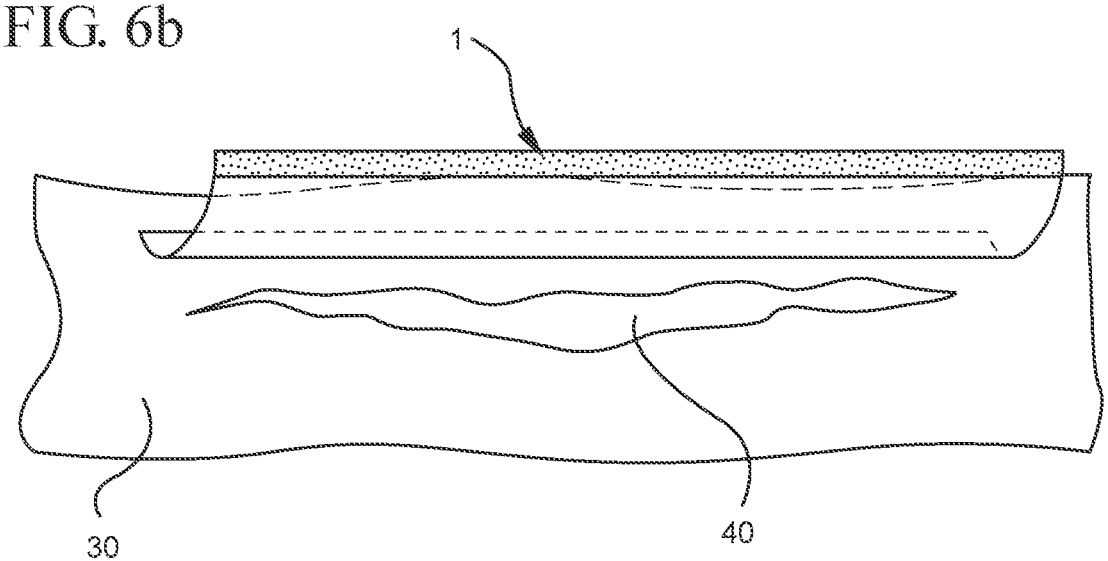

In a second step as shown in FIG. 6b, a length of flexible substrate is provided. Preferably, the length of flexible substrate is longer than the wound to be closed, and extends beyond opposite ends of the wound a sufficient distance to permit sufficient bonding. Thus, for example, the length of flexible material is preferably sufficient to extend at least ¼ inch, more preferably at least ½ inch or at least ¾ inch, and even more preferably at least one inch beyond each end of the wound. Furthermore, the flexible substrate is preferably wide enough to extend beyond each lateral edge of the wound throughout the length of the wound. The width of the flexible substrate is preferably wide enough that the entire wound is covered, with excess coverage, by the portion of the flexible substrate that is not previously coated with an adhesive substance for temporary bonding to the desired surface. That is, the uncoated portions of the flexible substrate preferably cover the full width of the wound, and extend beyond opposite lateral edges of the wound a sufficient distance to permit sufficient bonding. Thus, for example, the width of flexible substrate is preferably sufficient to extend at least ¼ inch, more preferably at least ½ inch or at least ¾ inch, and even more preferably at least one inch beyond each lateral edge of the wound.

In the second step, the previously applied adhesive substance on one edge of the flexible substrate is exposed. For example, the adhesive substance can be exposed either by applying the adhesive substance to the edge of the flexible substrate (or to the area of application adjacent the wound), or by removing a release layer covering the adhesive substance on the flexible substrate. The flexible substrate 1 is then applied to the arm or leg 30 at an area adjacent the wound 40, by applying the exposed adhesive substance to the arm or leg surface. If necessary, pressure can be applied to the flexible substrate 1 to help adhere the flexible substrate to the arm or leg 30.

Figure 6C:
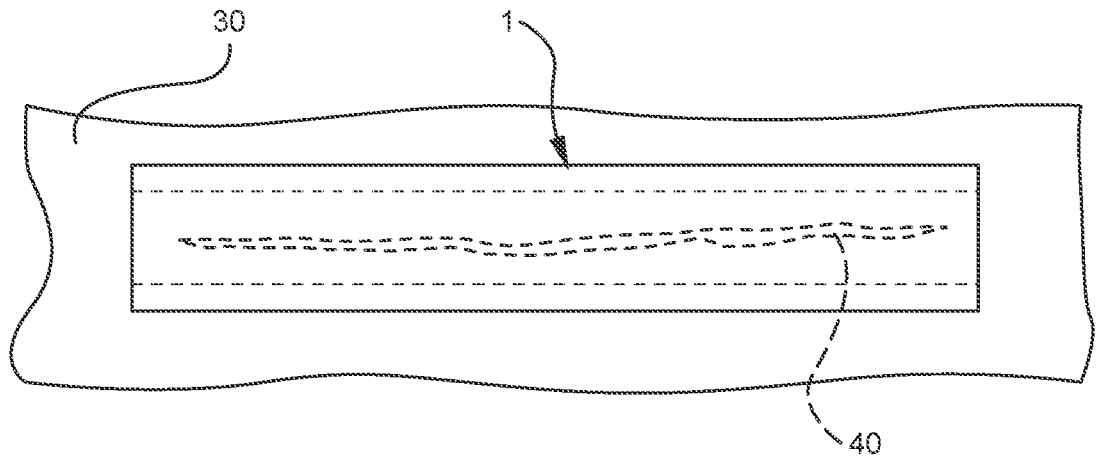

In a third step as shown by FIG. 6c, the opposite end of the flexible substrate is applied to the wound. Preferably, slight to moderate pressure is applied to opposite edges of the wound (such as by forceps, fingers, clamps, or the like) to approximate or appose the wound edges. Preferably, such approximation is conducted in a medically accepted manner, such as to as precisely as possible position the wound edges to help reduce subsequent scarring. With the wound edges approximated, the previously applied adhesive substance on the second edge of the flexible substrate is exposed. The remaining edge of the flexible substrate 1 is then applied to the arm or leg 30 at an area adjacent the wound 40, but opposite the wound 40 from the previously applied first edge of the flexible substrate 1, by applying the exposed adhesive substance to the arm or leg surface. If necessary, pressure can be applied to the flexible substrate 1 to help adhere the flexible substrate to the arm or leg 30.

Figure 6D:
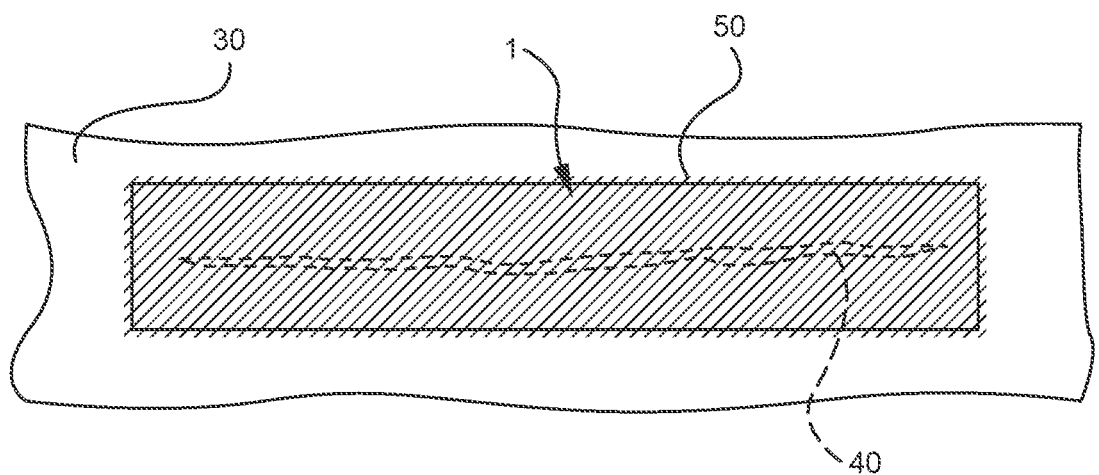

In a fourth step as shown by FIG. 6d, a polymerizable adhesive composition, such as a polymerizable monomeric adhesive composition 50, is applied over at least a portion of the surface of the flexible substrate 1. Preferably, the polymerizable adhesive composition 50 is applied to fully cover the surface of the flexible substrate 1. However, if desired, a lesser amount of the polymerizable adhesive composition can be used to conserve materials and assist in subsequent steps. In this instance, the polymerizable adhesive composition is preferably applied to the flexible substrate 1 at least in an area sufficient to cover the portion of the flexible substrate that will remain on the surface following completion of the application process. Thus, for example, where portions of the flexible substrate are to be removed as described in the following step 5, the polymerizable adhesive composition is applied to the flexible substrate to fully cover the non-removed portions. Alternatively, the polymerizable adhesive composition can be applied to only portions of the flexible substrate, such as only to portions overlying an underlying wound, or to portions overlying part, but not all, of the underlying wound.

In this step of applying the polymerizable adhesive composition, a sufficient amount of polymerizable adhesive composition should be applied to form the desired composite structure once the polymerizable adhesive composition has polymerized (or cured). Thus, for example, the amount of polymerizable adhesive composition should be sufficient to preferably allow the composition to penetrate through the flexible material to form a continuous coating between the arm or leg 30 and wound 40, and the flexible material of the flexible substrate 1, which continuous coating subsequently polymerizes or cures to form a continuous polymeric coating between the flexible substrate and the underlying surface. The quantity of polymerizable adhesive composition should preferably further allow for a quantity of the composition to remain in, and preferably over, the flexible substrate. This further amount of polymerizable adhesive composition polymerizes or cures with the remaining polymerizable adhesive composition to provide a unitary composite structure that is bonded to the underlying surface, such as the underlying surface of the arm or leg 30 and wound 40.

If necessary or desired, the step of applying polymerizable adhesive composition to the flexible substrate can be repeated one or more times. Thus, for example, a second or subsequent coating of the polymerizable adhesive composition can be applied, either prior or subsequent to complete curing of the underlying layer of polymerizable adhesive composition. Preferably, where multiple layers are to be applied, it is preferred that subsequent layers be applied after curing of the underlying layer has begin, but before curing is complete.

When applying the polymerizable adhesive composition to the flexible substrate, the polymerizable adhesive composition is preferably applied over an entire surface of the flexible substrate. That is, while the flexible substrate may provide some wicking, flowing, or capillary movement of the polymerizable adhesive composition within the bulk material of the flexible substrate, such wicking or capillary movement is minimal, and is not intended to provide complete coverage of the polymerizable adhesive composition over the flexible substrate. Thus, for example, it will generally not be possible to apply one or two drops of the polymerizable adhesive composition to the flexible substrate, and expect the polymerizable adhesive composition to completely cover the flexible substrate (unless, of course, the flexible substrate is such a small size that the drops substantially cover the surface). Rather, in embodiments of the present invention, the polymerizable adhesive composition is applied by dabbing, brushing, rolling, painting, swabbing or the like, the polymerizable adhesive composition onto the flexible substrate. If necessary, the applied polymerizable adhesive composition can be spread around on the surface of the flexible substrate to provide improved coverage.

Figure 6E:
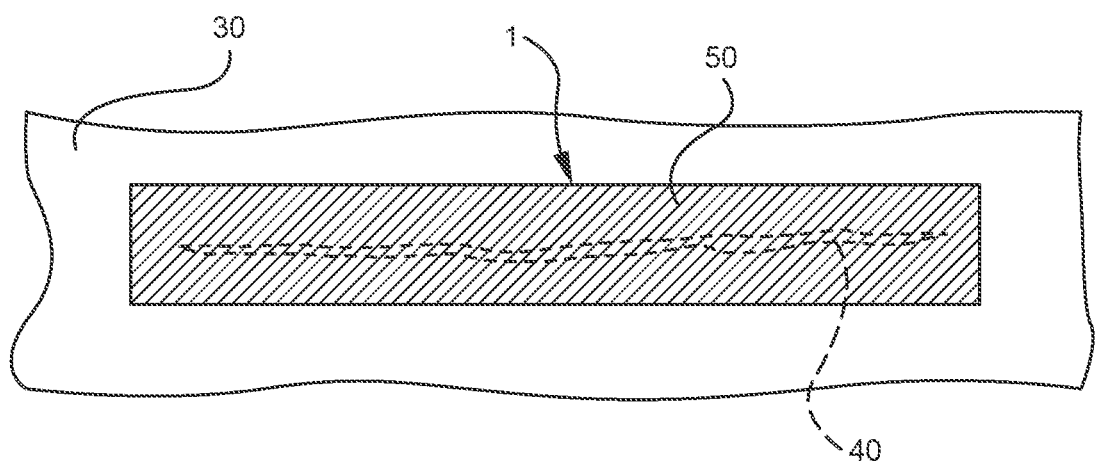

In a fifth step as shown in FIG. 6e, portions of the thus-formed composite structure are trimmed off, to provide a final composite structure covering the underlying wound. In this embodiment, the portions of the composite structure 1 corresponding to the portions of the flexible substrate 10 coated with the adhesive substance 20, are trimmed off. Such trimming may be preferred and/or required, for example, because the adhesive properties of the adhesive substance differ from the adhesive properties provided by the polymerizable adhesive composition. Where the adhesive substance 20 provides less adhesion than the polymerizable adhesive composition 50, it is likely that the portions adhered only by the adhesive substance 20 will prematurely separate from the underlying tissue. To prevent such premature separation, and resulting problems of lessened appearance and the like, these portions can be trimmed off after the polymerizable adhesive composition has cured.

Where the portions are to be trimmed off, such trimming can be conducted by any desired and suitable means. For example, the portions can be peeled back from the underlying surface, and trimmed using scissors, a knife, a scalpel, or the like. Alternatively, the flexible material used in forming the flexible substrate can be provided with one or more perforations or tear lines, to assist in the subsequent trimming operation.

To assist in the subsequent trimming operation, it is preferred that the adhesive substance applied to the underside of the flexible material be provided in such a manner that the polymerizable adhesive composition applied to the topside of the flexible substrate does not penetrate into or under the adhesive substance. That is, it is preferred that the relatively weaker adhesiveness provided by the adhesive substance, is not strengthened by interaction with the relatively stronger polymerizable adhesive composition. Preventing such interaction will assist in being able to peel back the flexible substrate in the areas of the adhesive substance to permit trimming of those portions. This interaction between the adhesive materials can be prevented, for example, by using adhesive materials that are not soluble in each other, by providing a substantially continuous coating of the adhesive substance on the desired portions of the flexible material, or the like. However, even if some interaction between the adhesive substance and the polymerizable adhesive composition does occur, the adhesive bond provided by the resultant combined adhesive may still be weak enough to permit trimming of the desired portions of the flexible substrate. Alternatively, if a bond is provided that is too strong to permit convenient trimming, then the portions of the flexible substrate having the adhesive substance can be retained on the application site, as the bond will tend not to prematurely separate and thus trimming of the portions may not be necessary.

A modification of the above-described process involves "rolling" or "taping" the flexible substrate onto the desired application site. In this embodiment, the flexible material is applied to the application site starting at one lengthwise end of the site, and straddling the width direction of the site, and progresses along the application site to the opposite lengthwise end of the site. This application is particularly useful, for example, when the application site is long and the flexible material is, for example, a length or roll of flexible material.

In a first step, the application site (e.g., arm or leg 30 having an open wound 40), is preferably first cleaned by removing excess exudates (blood or the like) to provide as dry a wound as possible to assist in wound closure.

In a second step, a length of flexible substrate is provided. Preferably, the length of flexible substrate is longer than the wound to be closed, and extends beyond opposite ends of the wound a sufficient distance to permit sufficient bonding. Thus, for example, the length of flexible material is preferably sufficient to extend at least ¼ inch, more preferably at least ½ inch or at least ¾ inch, and even more preferably at least one inch beyond each end of the wound. Furthermore, the flexible substrate is preferably wide enough to extend beyond each lateral edge of the wound throughout the length of the wound. The width of the flexible substrate is preferably wide enough that the entire wound is covered, with excess coverage, by the portion of the flexible substrate that is not previously coated with an adhesive substance for temporary bonding to the desired surface. That is, the uncoated portions of the flexible substrate preferably cover the full width of the wound, and extend beyond opposite lateral edges of the wound a sufficient distance to permit sufficient bonding. Thus, for example, the width of flexible substrate is preferably sufficient to extend at least ¼ inch, more preferably at least ½ inch or at least ¾ inch, and even more preferably at least one inch beyond each lateral edge of the wound.

In the second step, the previously applied adhesive substances on the edges of one lengthwise end of the flexible substrate are exposed. For example, the adhesive substances can be exposed either by applying the adhesive substance to the edges of the flexible substrate (or to the areas of application adjacent the wound), or by removing release layers coving the adhesive substance on the flexible substrate. The flexible substrate is then applied to the application site at areas adjacent the wound, by applying one of the exposed adhesive substances to the arm or leg surface on one side of the wound and the other of the exposed adhesive substances to the arm or leg surface on opposite lateral side of the wound. If necessary, pressure can be applied to the flexible substrate to help adhere the flexible substrate to the application site.

In this second step, prior to applying the second edge or second adhesive substance, however, the wound edges are preferably approximated. Thus, for example, one hand can be used to approximate the wound edges, as the other hand is used to apply the flexible material. For example, slight to moderate pressure can be applied to opposite edges of the wound (such as by forceps, fingers, clamps, or the like) to approximate or appose the wound edges. As above, such approximation is preferably conducted in a medically accepted manner, such as to as precisely as possible position the wound edges to help reduce subsequent scarring.

In a third step, application of the flexible substrate continues along the length of the application site. For example, application can continue by "rolling" or "taping" the flexible material onto the application site, progressing from one lengthwise end of the site to the other lengthwise end. Preferably, or if necessary, lateral edges of the wound at the application site can be approximated in the manner described above as the flexible material is applied in the lengthwise direction.

In a fourth step, a polymerizable adhesive composition, such as a polymerizable monomeric adhesive composition, is applied over the surface of the flexible substrate. The polymerizable adhesive composition can be applied in the same manner as described above, and thus the details are not repeated here.

In a fifth step, portions of the thus-formed composite structure can be trimmed off, if desired, to provide a final composite structure covering the underlying wound. The trimming likewise can be conducted in the same manner as described above, and thus the details are not repeated here.

A particular advantage of this application method, as compared to the first application method described above, is that the method is particularly well suited for longer wounds or longer application sites. Once a first end of the flexible substrate is applied to the wound, the remaining length of the flexible substrate is applied by rolling or taping the flexible substrate in place, with gradual approximation of wound edges as necessary. Where wounds or application sites are long, this method is well suited for use by a single individual, as assistance in applying the flexible substrate may not be required.

Of course, although two application methods are described above, other methods will be readily apparent to those skilled in the art. The application methods are In no way limited to the methods described above.

Figure 7A:
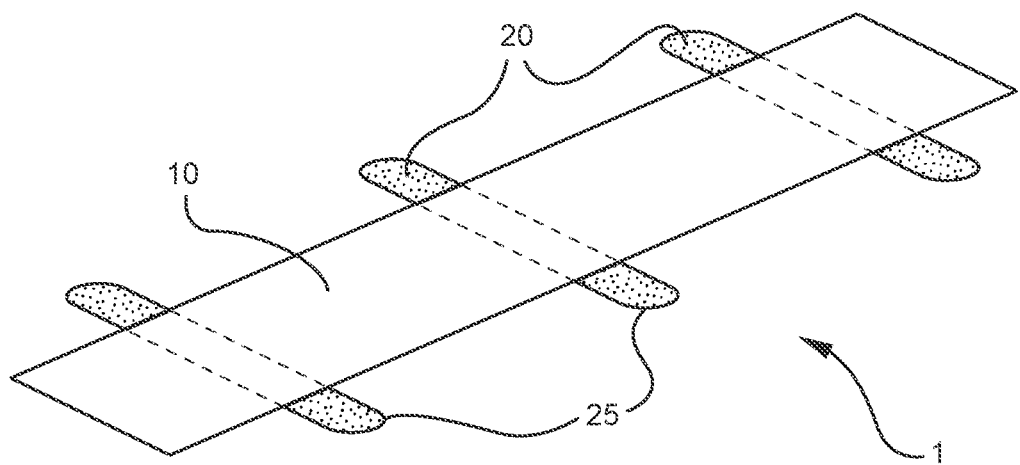
FIG. 7a is a perspective view of another embodiment of the present invention.
Figure 7B:
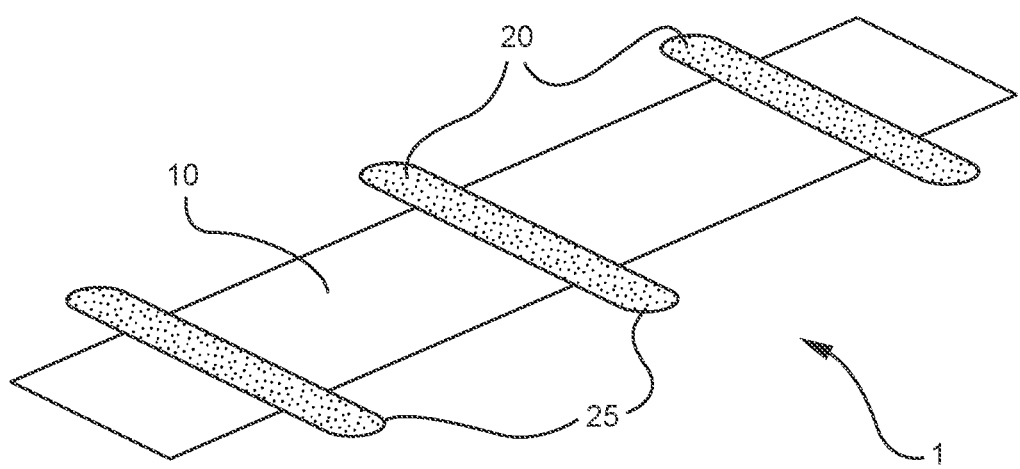

A still further embodiment of the present invention is shown in FIGS. 7a and 7b. In this embodiment, the flexible substrate 1 includes a flexible material 10, as described above. However, instead of applying the adhesive substance 20 directly to the bottom side of the flexible material 10, the adhesive substance 20 is applied to bottom sides of one or more adhesive strips, such as pressure sensitive adhesive strips 25. The adhesive strips 25 can then be suitably located either on the bottom (application site contacting) side of the flexible material 10 (as shown in FIG. 7a), or on the top (exposed) side of the flexible material 10 (as shown in FIG. 7b).

In these embodiments, the adhesive substance 20 applied to the adhesive strips 25 can extend across the entire length of the adhesive strip, such as shown in FIG. 7b, or only across one or more portions of the adhesive strip, such as shown in FIG. 7a. Applying the adhesive substance 20 across the entire length of the adhesive strip 25 is useful, for example, when the adhesive strip is being applied to the top (exposed) side of the flexible material 10. In this embodiment, the adhesive substance serves two purposes—adhering the adhesive strip to the flexible material, and adhering the flexible substrate (composite flexible material and adhesive substance) to the application site prior to application of the polymerizable adhesive composition. Alternatively, the adhesive substance can be provided on only one or more portions of the adhesive strip, for example, where it is desired to provide as much surface area as possible for application and setting of the polymerizable adhesive composition. It will be understood that where the adhesive strips 25 are provided on the bottom side of the flexible material 10, the adhesive substance can be provided on both sides of the adhesive strip, so that one side can be adhered to the flexible material while the other side provides adhesion to the application site.

Figure 7C:
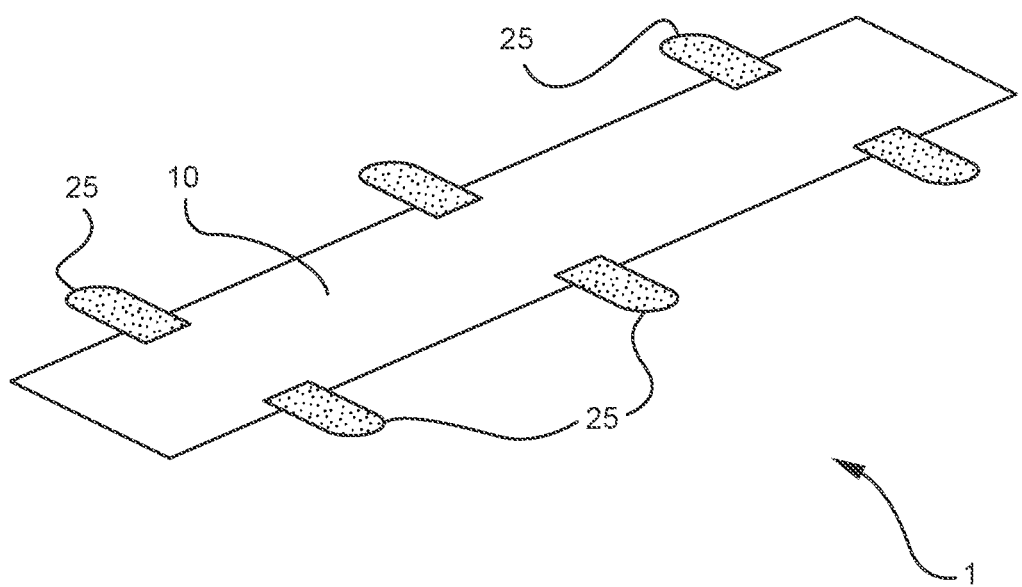
FIG. 7c is a perspective view of a further embodiment of the present invention shown in FIG. 7b.

An alternative to this embodiment is shown in FIG. 7c. FIG. 7c represents a modification of the embodiment of FIG. 7b, but where the adhesive strips 25 do not extend completely across the flexible material 10. In this embodiment, the adhesive strips are attached to sides of the flexible material 10, but do not traverse the flexible material 10. As described above, the adhesive strips could be located either on the top or bottom sides of the flexible material 10, as desired.

When these latter embodiments of the flexible substrate are used, the flexible substrate can be applied substantially by the methods described above. That is, the flexible substrate can be applied by exposing the adhesive substance and applying the flexible substrate to the application site. Once the polymerizable adhesive composition is applied and set, the adhesive strips can be trimmed off or retained, as desired. Other modification of these embodiments will also be apparent to those skilled in the art.

As described above, one or more chemical substances may be applied to the flexible substrate, which can subsequently chemically or physically interact with an applied polymerizable adhesive composition. Such chemical substances can include, for example, one or more polymerization initiators or rate modifiers, one or more bioactive materials, and combinations thereof.

Suitable polymerization and/or cross-linking initiators and rate modifiers, and methods for applying them to substrates, are described in, for example, U.S. Pat. Nos. 5,928,611, 6,352,704, 6,455,064, 6,579,469 and 6,595,940 and U.S. patent application Ser. No. 09/430,177, filed Oct. 29, 1999, Ser. Nos. 09/430,289 09/430,180 filed Oct. 29, 1999; Ser. No. 09/385,030 filed Aug. 30, 1999; and Ser. No. 09/176,889 filed Oct. 22, 1998, the entire disclosures of which are incorporated herein by reference. Preferred initiators for some medical uses include benzalkonium chloride, and for some industrial uses include dimethyl toluidine.

Particular initiators and rate modifiers for particular monomers may be readily selected by one of skill in the art without undue experimentation. Control of the molecular weight distribution of the applied adhesive can be enhanced by selection of the concentration and functionality of the initiator or rate modifier vis-a-vis the selected monomer. Suitable polymerization initiators and rate modifiers for cyanoacrylate compositions include, but are not limited to, detergent compositions; surfactants, including nonionic surfactants such as polysorbate 20 product (e.g., Tween 20™ product; ICI Americas), polysorbate 80 product (e.g., Tween 80™ product; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide.

In preferred embodiments, the initiator may be a bioactive material that possesses antiviral, antimicrobial, antifungal and/or wound healing properties. An example of such a material that possesses polymerization initiation and antiviral, antimicrobial, and/or antifungal properties is Gentian Violet, also known as crystal violet or methylrosaniline chloride. Examples of materials that possess polymerization initiation and wound healing properties also include various zinc complexes and zinc salts, antioxidants such as vitamin E and other vitamins and the like, and copper compounds such as copper chloride, copper sulfate and copper peptides. Such materials are particularly preferred because they can serve not only as the polymerization initiator or rate modifier for the cyanoacrylate monomer, they can also provide additional benefits to the wound site, such as antiviral effects, antimicrobial effects and/or antifungal effects or help to promote wound healing.

When zinc compounds are present, the zinc compound can be present in various forms, such as zinc salts. For example, suitable zinc compounds include, but are not limited to, zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, mixtures thereof, and the like. Preferably, the zinc compounds are of $Zn^{2+}$. Incorporation of such zinc compounds into the applied cyanoacrylate composition, either prior to or concurrent with application and/or initiation, is particularly effective in promoting wound healing of leg ulcers, thermal burns, and the like.

The polymerizable and/or cross-linkable material may also contain an initiator and/or a rate modifier which is inactive until activated by a catalyst or accelerator (included within the scope of the term "initiator" as used herein). Initiators activated by stimulation such as heat and/or light (e.g., ultraviolet or visible light) are also suitable if the flexible substrate is appropriately subjected to such stimulation.

In addition to the polymerization and/or cross-linking initiator and/or rate modifier, the flexible substrate can also include various other materials that may or may not act as a polymerization initiator and/or rate modifier. For example, the flexible substrate can include a bioactive material, which may or may not also be a polymerization and/or cross-linking initiator and/or rate modifier. Examples of suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Thus, in embodiments, the initiator and/or the rate modifier can be, but does not have to be, bioactive. In embodiments where the initiator and/or the rate modifier is bioactive, the method of the invention can be used to close, cover, or protect tissue and wounds while simultaneously providing a bioactive material to the tissue or wound.

Suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Such compounds include, but are not limited to, acetic acid, aluminum acetate, bacitracin, bacitracin zinc, benzalkonium chloride, benzethonium chloride, betadine, calcium chloroplatinate, certrimide, cloramine T, chlorhexidine phosphanilate, chlorhexidine, chlorhexidine sulfate, chloropenidine, chloroplatinatic acid, ciprofloxacin, clindamycin, clioquinol, cysostaphin, gentamicin sulfate, hydrogen peroxide, iodinated polyvinylidone, iodine, iodophor, minocycline, mupirocin, neomycin, neomycin sulfate, nitrofurazone, nononynol 9, potassium permanganate, penicillin, polymycin, polymycin B, polymyxin, polymyxin B sulfate, polyvinylpyrrolidone iodine, povidone iodine, 8-hydroxyquinoline, quinolone thioureas, rifampin, rifamycin, copper chloride, copper sulfate, copper peptides, silver acetate, silver benzoate, silver carbonate, silver chloride, silver citrate, silver iodide, silver nitrate, silver oxide, silver sulfate, sodium chloroplatinate, sodium hypochlorite, sphingolipids, tetracycline, zinc oxide, salts of sulfadiazine (such as silver, sodium, and zinc), antioxidants such as vitamins such as vitamin E, other agents mentioned above, and mixtures thereof. Preferable bioactive materials are USP approved, more preferably USP monographed.

The polymerization and/or cross-linking initiator and/or rate modifier, and/or the bioactive material, may be applied to the flexible substrate by any suitable means, including, but not limited to, spraying, dipping, injecting, or brushing the flexible substrate with a liquid medium containing the material to be applied.

As mentioned above, the composite structure is formed by applying a polymerizable adhesive composition to the flexible substrate, and allowing the polymerizable adhesive composition to polymerize.

The polymerizable (i.e., monomer and/or prepolymeric) adhesive composition may include one or more polymerizable monomers, which preferably are synthetic or semi-synthetic monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687, 5,928,611 and 6,183,593, U.S. patent application Ser. No. 09/430,177, filed on Oct. 29, 1999, and U.S. Pat. No. 6,183,593, which are hereby incorporated in their entirety by reference herein.

Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms.

The α-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

Preferred α-cyanoacrylate monomers used in this invention include methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate.

Other suitable cyanoacrylates for use in the present invention also include, but are not limited to, alkyl ester cyanoacrylate monomers such as those having the formula

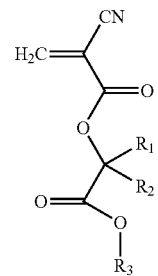

wherein $R_1$ and $R_2$ are, independently H, a straight, branched or cyclic alkyl, or are combined together in a cyclic alkyl group, and $R_3$ is a straight, branched or cyclic alkyl group. Preferably, $R_1$ is H or a $C_1$, $C_2$ or $C_3$ alkyl group, such as methyl or ethyl; $R_2$ is H or a $C_1$, $C_2$ or $C_3$ alkyl group, such as methyl or ethyl; and $R_3$ is a $C_1$-$C_{16}$ alkyl group, more preferably a $C_1$-$C_{10}$ alkyl group, such as methyl, ethyl, propyl, butyl, pentyl, hexyl, heptyl, octyl, nonyl or decyl, and even more preferably a $C_2$, $C_3$ or $C_4$ alkyl group. Such alkyl ester cyanoacrylates and other suitable monomers are disclosed in, for example, U.S. patent application Ser. No. 09/919,877, filed Aug. 2, 2001, and U.S. Pat. No. 6,620,846, the entire disclosures of which are incorporated herein by reference.

Examples of preferred alkyl ester cyanoacrylates include, but are not limited to, butyl lactoyl cyanoacrylate (BLCA), butyl glycoloyl cyanoacrylate (BGCA), ethyl lactoyl cyanoacrylate (ELCA), and ethyl glycoloyl cyanoacrylate (EGCA). BLCA may be represented by the above formula, wherein $R_1$ is H, $R_2$ is methyl and $R_3$ is butyl. BGCA may be represented by the above formula, wherein $R_1$ is H, $R_2$ is H and $R_3$ is butyl. ELCA may be represented by the above formula, wherein $R_1$ is H, $R_2$ is methyl and $R_3$ is ethyl. EGCA may be represented by the above formula, wherein $R_1$ is H, $R_2$ is H and $R_3$ is ethyl.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane and others as listed in U.S. Pat. No. 6,183,593, the disclosure of which is incorporated in its entirety by reference herein.

In embodiments, the composition may also include one or more polymerization initiators or rate modifiers. Although the polymerization initiator or rate modifier is described above as being incorporated into or onto the flexible material, it is also possible for the polymerization initiator or rate modifier to be incorporated directly into the polymerizable adhesive composition. In such embodiments, the polymerization initiator or rate modifier is mixed with the polymerizable adhesive composition preferably immediately prior to or concurrent with application of the polymerizable adhesive composition to the flexible substrate. For example, the polymerization initiator or rate modifier and polymerizable adhesive composition can be mixed prior to application by suitable mixing devices in an applicator itself or in a separate container, or they can be mixed concurrent with application by mixing as the polymerizable adhesive material is expressed form an applicator. Any suitable polymerization initiators or rate modifiers, including those described above, can be used in these embodiments.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. Nos. 4,720,513, and 6,310,166, the disclosures of which are hereby incorporated in their entireties by reference herein.

The composition may optionally also include thickeners. Suitable thickeners may include poly (2-ethylhexy methacrylate), poly(2-ethylhexyl acrylate) and others as listed in U.S. Pat. No. 6,183,593, the disclosure of which is incorporated by reference herein in its entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-microbial agents, such as, for example, various acidic anti-microbials, as identified above.

The compositions may also include pH modifiers to control the rate of degradation of the resulting polymer, as disclosed in U.S. Pat. No. 6,143,352, the entire disclosure of which is hereby incorporated by reference herein in its entirety.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference. Such preservatives can be in addition to any anti-microbial agent that may or may not be added to the composition. Such preservatives can be included irrespective of whether the composition and containers are sterilized.

In embodiments, the materials and processes of the present invention provide significant advantages over the current materials and methods for wound closure. These advantages include, among others, improved wound closure, provision of an improved durable microbial barrier, reduced procedure time, improved cosmesis, less pain (during staple/suture removal) resulting in increased patient satisfaction, and improved financial/economic outcomes by eliminating follow-up visits for staple/suture removal.

The materials and processes of the present invention provide improved wound closure. Because the composite structure provides a flexible polymeric covering over the wound site, it provides a degree of tension to assist in closing the wound and maintain the wound closed. By a combination of the flexible material within the composite structure, and the rigidity and adhesion provided by polymerization of the polymerizable adhesive composition, the composite structure provides improved strength, decreases wound dehiscence, and assists healing.

The materials and processes of the present invention also provide an improved microbial barrier. Because the composite structure fully covers the wound, microbial transport into and out of the wound are decreased. This in turn helps battle or prevent infection, in turn resulting in faster wound healing.

The materials and processes of the present invention also provide improved cosmesis. Such cosmesis benefits includes improved cosmetic appearances both during and after the wound healing process. For example, during wound healing, the composite structures of the present invention provide decreased dressing bulk and thickness and improved appearance. Furthermore, because the composite structures permit more precise and sustained wound approximation, the composite structures can provide decreased scar appearance, such as in terms of scar width, scar tissue height, scar coloration, and the like.

Related to the above advantages, the materials and processes of the present invention provide increased patient satisfaction. Increased satisfaction is provided, for example, due to the improved "feel" of the wound dressing, the improved cosmetic results, and improved assurance of wound closure and dressing strength, and the like. In addition, because of the strong bond provided, the composite structure of the present invention is expected to remain in place over an external wound for about 10 to 14 days, although shorter or longer times may be provided. During that time, the patient can bathe without worrying about water and contaminants entering the wound through the dressing. Furthermore, because staple or suture removal is not required, the patient experiences less pain and anticipation, improving the healing experience.

The present invention is thus applicable to a wide range of treatments, including wound treatment and other medical procedures. For example, the present invention can be used as a replacement for, or in addition to, sutures or staples to join together two surfaces. The invention can also be used to coat, protect, or otherwise cover surface, superficial, internal, or topical wounds including, but not limited to, minor cuts, scrapes, irritations, compromised skin, superficial lacerations, abrasions, burns, sores, and stomatitis. The methods of the invention can also be used on tissues that do not show any signs of tissue damage. For example, the methods can be used to deliver medicaments to a patient through healthy tissue. They can also be used, for example, to locally deliver medicaments to tissues such as tumors or organs.

Specific embodiments of the invention will now be described in detail. These Examples are intended to be illustrative, and the invention is not limited to the materials, conditions, or process parameters set forth in these embodiments. All parts and percentages are by weight unless otherwise indicated.

EXAMPLES

Preparation of Flexible Substrate Material:

A length of polypropylene mesh material is obtained having a length of about four feet and a width of about 1¾ inches. The polypropylene mesh is dipped into a solution of benzalkonium chloride and acetone, to adsorb the benzalkonium chloride on the polypropylene mesh. The mesh is subsequently dried to volatilize and remove the acetone solvent. To a backside of the mesh, a conventional pressure sensitive adhesive is applied as a continuous layer along the 4-foot length of the mesh, and extending about ⅜ inch from each edge, thus leaving a 1 inch strip along the center of the length of the mesh that is not covered by the adhesive substance. The applied pressure sensitive adhesive is subsequently covered by respective 4-foot by ⅜ inch strips of release paper. The thus-produced flexible substrate is used in the following Examples.

Example 1

A patient is presented having a one inch cut on the arm. The cut does not extend fully through the dermal layers of the skin.

Following suitable washing, disinfecting and drying of the area around the cut, a 2-inch length of the prepared flexible substrate is applied to the wound site. The flexible substrate is applied by first removing one of the two release strip papers and affixing the pressure sensitive adhesive edge to one side of the cut, about ⅞ inch from the edge of the cut. The second release strip paper is then removed from the flexible substrate. After approximating the wound edges using slight pressure applied by two fingers, the remaining pressure sensitive adhesive edge of the flexible substrate is applied to the other side of the cut, about ⅞ inch from the edge of the cut. The flexible substrate extends about ½ inch beyond each end of the wound.

A quantity of a stabilized 2-octyl cyanoacrylate adhesive is applied to the exposed surface of the flexible substrate, and is spread to permeate into and fully cover the flexible substrate. Polymerization of the composition proceeds in about 1 minute. After complete polymerization, the edges of the flexible substrate adhered to the tissue using pressure sensitive adhesive are peeled back, and those portions of the flexible substrate are removed by trimming with surgical scissors. The result is a firmly bonded composite structure, bonded to the skin over the full area of the cut.

The composite structure remains in place for about 10 to 14 days, during which time the wound heals.

Example 2

A patient is presented having a four inch cut on the leg. The cut extends fully through the dermal layers of the skin.

Following suitable washing, disinfecting and drying of the area around the cut, subcutaneous dissolvable sutures are used to approximate and close the subcutaneous layers in the wound. Next, a 5-inch length of the prepared flexible substrate is applied to the wound site. The flexible substrate is applied by first removing one of the two release strip papers and affixing the pressure sensitive adhesive edge to one side of the cut, about ⅞ inch from the edge of the cut. The second release strip paper is then removed from the flexible substrate. After approximating the wound edges using slight pressure applied by the hands, the remaining pressure sensitive adhesive edge of the flexible substrate is applied to the other side of the cut, about ⅞ inch from the edge of the cut. The flexible substrate extends about ½ inch beyond each end of the wound.

A quantity of a stabilized 2-octyl cyanoacrylate adhesive is applied to the exposed surface of the flexible substrate, and is spread to permeate into and fully cover the flexible substrate. Polymerization of the composition proceeds in about 1 minute. After complete polymerization, the edges of the flexible substrate adhered to the tissue using pressure sensitive adhesive are peeled back, and those portions of the flexible substrate are removed by trimming with surgical scissors. The result is a firmly bonded composite structure, bonded to the skin over the full area of the laceration.

The composite structure remains in place for about 10 to 14 days, during which time the cut heals.

Comparative Example 1

A patient is presented having a four inch cut on the leg, substantially similar to the laceration of the patient in Example 2. The cut extends fully through the dermal layers of the skin.

Following suitable washing, disinfecting and drying of the area around the cut, subcutaneous dissolvable sutures are used to approximate and close the subcutaneous layers in the wound, in a similar manner to Example 2. Next, conventional sutures and staples are used to close the surface layers of the wound. The wound is subsequently covered by gauze pads and an ace bandage to control residual bleeding.

The wound dressing is maintained in place for about 10 to 14 days, being changed several times over that period to provide clean gauze. After the dressing is removed, the sutures and staples on the surface of the skin are removed.

A comparison of the results of Example 2 and Comparative Example 1 indicate that healing of the wounds is substantially identical. However, the results of Example 2 indicate an improvement in wound appearance, with less evident skin trauma. The patient in Example 2 also reports increased comfort in initial dressing application, in appearance and feeling over the intervening 10-14 days, and in removal of the dressing.

While the invention has been described with reference to preferred embodiments, the invention is not limited to the specific examples given, and other embodiments and modifications can be made by those skilled in the art without departing from the spirit and scope of the invention.

What is claimed is:

1. A method of bonding tissue, comprising: placing at least one strip of flexible material over a section of tissue, wherein said flexible material comprises a polymerization initiator or rate modifier disposed in or on said flexible material, and an adhesive substance disposed on at least a portion of a bottom side of said flexible material; applying a polymerizable adhesive composition over at least a portion of a top surface of the flexible material; and allowing the polymerizable adhesive composition to permeate into and under the flexible material and polymerize to bond the flexible material to said tissue.

2. The method of claim 1, wherein the flexible material is a mesh.

3. The method of claim 2, wherein the mesh is formed of either woven or non-woven fabrics or materials.

4. The method of claim 1, wherein the polymerization initiator or rate modifier is selected from the group consisting of detergent compositions, nonionicsurfactants, cationic surfactants, anionic surfactants, stannous octoate (tin (II) 2-ethylhexanoate), sodium tetradecyl sulfate, amphoteric or zwitterionic surfactants, amines, imines, amides, phosphines, phosphates, phosphonium salts, alcohols, methyl gallate, ascorbic acid, tannins, tannic acid, inorganic bases and salts, sulfur compounds, polymeric cyclic ethers, cyclic and acyclic carbonates, phase transfer catalysts, organometallics, manganese acetylacetonate, radical initiators and radicals, and bioactive compounds or agents.

5. The method of claim 4, wherein the polymerization initiator is one or more quaternary ammonium halide(s).

6. The method of claim 5, wherein the polymerization initiator is one or more alkylbenzyldimethylammonium chloride(s) having an alkyl ranging from 6-18 carbon atoms.

7. The method of claim 5 wherein the polymerization initiator comprises benzethonium chloride.

8. The method of claim 5, wherein the polymerizable adhesive composition is a monomeric composition.

9. The method of claim 8, wherein polymerizable adhesive composition comprises one or more 1,1-disubstituted ethylene monomers.

10. The method of claim 9, wherein polymerizable adhesive composition comprises one or more monomer selected from the group consisting of methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, butyl lactoyl cyanoacrylate, butyl glycolcyl cyanoacrylate, ethyl lactoyl cyanoacrylate, and ethyl glycoloyl cyanoacrylate.

11. The method of claim 5 wherein the polymerization initiator comprises benzalkonium chloride.

12. The method of claim 1, wherein polymerizable adhesive composition comprises one or more 1,1-disubstituted ethylene monomers.

13. The method of claim 12, wherein polymerizable adhesive composition comprises one or more monomer selected from the group consisting of methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, butyl lactoyl cyanoacrylate, butyl glycolcyl cyanoacrylate, ethyl lactoyl cyanoacrylate, and ethyl glycoloyl cyanoacrylate.

14. The method of claim 1, wherein the flexible material comprises a polyester mesh, the polymerization initiator comprises benzethonium chloride, the adhesive substance comprises a pressure sensitive adhesive, and the polymerizable adhesive composition comprises 2-octyl cyanoacrylate monomer.

15. The method of claim 1, wherein the step of applying the polymerizable adhesive is applied to a portion of the flexible material overlying an underlying wound.

16. The method of claim 1, wherein the step of applying the polymerizable adhesive is applied to a part of a portion of the flexible material overlying an underlying wound.

17. The method of claim 1, wherein the flexible material comprises a polyester mesh, the polymerization initiator comprises benzalkonium chloride, the adhesive substance comprises a pressure sensitive adhesive, and the polymerizable adhesive composition comprises 2-octyl cyanoacrylate monomer.

18. A method of bonding tissue, comprising:
    placing at least one strip of flexible material over a section of tissue, wherein said flexible material comprises a polymerization initiator or rate modifier disposed in or on said flexible material;
    applying at least one adhesive strip on the flexible material and contacting the tissue;
    applying a polymerizable adhesive composition over at least a portion of a top surface of the flexible material; and allowing the polymerizable adhesive composition to permeate into and under the flexible material and polymerize to bond the flexible material to said tissue.

19. The method of claim 18, wherein the at least one adhesive strip is applied across the flexible material and contacts the tissue.

20. The method of claim 18, wherein at least two adhesive strips are applied on the flexible material and contact the tissue.

21. The method of claim 20, wherein the at least two adhesive strips are applied across the flexible material and contact the tissue.

22. The method of claim 21, wherein at least one of the adhesive strips is placed toward a first end of the flexible material and the at least second of the adhesive strips is placed toward a second end of the flexible material.

23. The method of claim 20, wherein at least one of the adhesive strips is placed toward a first end of the flexible material and the at least second of the adhesive strips is placed toward a second end of the flexible material.

24. The method of claim 18, wherein the step of applying the polymerizable adhesive is applied to a portion of the flexible material overlying an underlying wound.

25. The method of claim 18, wherein the flexible material comprises a polyester mesh, the polymerization initiator comprises benzethonium chloride, the adhesive substance comprises a pressure sensitive adhesive, and the polymerizable adhesive composition comprises 2-octyl cyanoacrylate monomer.

26. The method of claim 18, wherein the flexible material comprises a polyester mesh, the polymerization initiator comprises benzalkonium chloride, the adhesive substance comprises a pressure sensitive adhesive, and the polymerizable adhesive composition comprises 2-octyl cyanoacrylate monomer.

27. The method of claim 18, wherein the step of applying the polymerizable adhesive is applied to a part of a portion of the flexible material overlying an underlying wound.

\* \* \* \* \*